United States Patent
Bedi et al.

(10) Patent No.: US 12,268,552 B2
(45) Date of Patent: Apr. 8, 2025

(54) METHOD AND APPARATUS FOR THE AUTOMATIC DETECTION OF ATHEROMAS IN PERIPHERAL ARTERIES

(71) Applicant: Atherosys, Inc., Issaquah, WA (US)

(72) Inventors: Ram L. Bedi, Issaquah, WA (US); Todor Jeliaskov, Scottsdale, AZ (US); Charles D. Emery, Gilbert, AZ (US)

(73) Assignee: Atherosys, Inc., Issaquah, WA (US)

( * ) Notice: Subject to any disclaimer, the term of this patent is extended or adjusted under 35 U.S.C. 154(b) by 311 days.

(21) Appl. No.: 17/084,299

(22) Filed: Oct. 29, 2020

(65) Prior Publication Data
US 2021/0045710 A1 Feb. 18, 2021

Related U.S. Application Data

(63) Continuation of application No. PCT/US2019/029739, filed on Apr. 29, 2019.
(Continued)

(51) Int. Cl.
*A61B 8/08* (2006.01)
*A61B 8/00* (2006.01)
(Continued)

(52) U.S. Cl.
CPC .............. *A61B 8/0891* (2013.01); *A61B 8/02* (2013.01); *A61B 8/06* (2013.01); *A61B 8/085* (2013.01);
(Continued)

(58) Field of Classification Search
CPC ........... A61B 8/0891; A61B 8/02; A61B 8/06; A61B 8/085; A61B 8/485; A61B 8/488;
(Continued)

(56) References Cited

U.S. PATENT DOCUMENTS 4,945,478 A * 7/1990 Merickel ................... G06T 7/00
382/131
5,954,653 A 9/1999 Hatfield et al.
(Continued)

FOREIGN PATENT DOCUMENTS

| CN | 106388867 A | 2/2017 |
|---|---|---|
| EP | 2163202 | 3/2010 |

(Continued)

OTHER PUBLICATIONS

Molinari F, Zeng G, Suri JS. A state of the art review on intima-media thickness (IMT) measurement and wall segmentation techniques for carotid ultrasound. Comput Methods Programs Biomed. Dec. 2010;100(3):201-21. doi: 10.1016/j.cmpb.2010.04.007. Epub May 15, 2010. PMID: 20478640 (Year: 2010).*

(Continued)

*Primary Examiner* — John D Li
(74) *Attorney, Agent, or Firm* — Perkins Coie LLP

(57) ABSTRACT

A method for detecting the presence of an atheroma in an artery of interest using an ultrasound apparatus can include performing a first procedure on a first day. The first procedure can include detecting one or more blood vessels in a target region of a patient's body. The procedure can include identifying, from the one or more blood vessels, an artery of interest; automatically detecting spatial boundaries of constituent layers of an arterial wall of the artery of interest and calculating, via a processor of the ultrasound apparatus, a cross-sectional intima-media area (IMA) of the artery of interest at a first location along a length of the artery of interest. The procedure can include automatically calculating, via the processor of the ultrasound apparatus, IMA of the artery of interest at a second or more locations along the length of the artery of interest. In some embodiments, the procedure includes automatically calculating, via the processor and based at least in part on the calculations of the (Continued)

IMAs of the artery of interest at the first location and at the second or more locations, an intima-media volume (IMV), arterial volume, and luminal volume of the artery of interest over a predetermined length of the artery of interest.

32 Claims, 30 Drawing Sheets

Related U.S. Application Data

(60) Provisional application No. 62/664,616, filed on Apr. 30, 2018.

(51) Int. Cl.
  *A61B 8/02* (2006.01)
  *A61B 8/06* (2006.01)
  *G16H 30/40* (2018.01)
  *G16H 50/20* (2018.01)

(52) U.S. Cl.
  CPC .............. *A61B 8/485* (2013.01); *A61B 8/488* (2013.01); *A61B 8/5223* (2013.01); *A61B 8/5269* (2013.01); *G16H 30/40* (2018.01); *G16H 50/20* (2018.01)

(58) Field of Classification Search
  CPC .... A61B 8/5223; A61B 8/5269; G16H 50/20; G16H 30/40
  USPC ........................................................ 600/408
  See application file for complete search history.

(56) References Cited

U.S. PATENT DOCUMENTS

| | | | |
|---|---|---|---|
| 6,023,968 A * | 2/2000 | Spratt | G01F 1/663 73/204.14 |
| 6,139,496 A | 10/2000 | Chen et al. | |
| 6,537,220 B1 | 3/2003 | Friemel et al. | |
| 6,695,784 B1 | 2/2004 | Michaell | |
| 7,356,367 B2 | 4/2008 | Liang et al. | |
| 7,569,016 B2 | 8/2009 | Watanabe et al. | |
| 7,925,064 B2 | 4/2011 | Cloutier et al. | |
| 8,075,488 B2 | 12/2011 | Burton | |
| 8,167,805 B2 | 5/2012 | Emery et al. | |
| 8,491,484 B2 | 7/2013 | Lewis | |
| 8,687,862 B2 * | 4/2014 | Hsu | G06T 7/0012 382/128 |
| 8,740,796 B2 | 6/2014 | Fukumoto et al. | |
| 9,179,889 B2 | 11/2015 | Fukumoto et al. | |
| 9,192,352 B2 | 11/2015 | Yao et al. | |
| 9,220,477 B2 | 12/2015 | Urabe et al. | |
| 9,357,980 B2 | 6/2016 | Toji et al. | |
| 9,498,185 B2 | 11/2016 | Kimoto et al. | |
| 9,693,755 B2 | 7/2017 | Kondoh | |
| 9,770,227 B2 | 9/2017 | Kawabata et al. | |
| 10,722,209 B2 | 7/2020 | Chen et al. | |
| 11,771,399 B2 | 10/2023 | Bedi et al. | |
| 2004/0116813 A1 * | 6/2004 | Selzer | A61B 8/463 600/467 |
| 2005/0096528 A1 | 5/2005 | Fritz et al. | |
| 2005/0182319 A1 * | 8/2005 | Glossop | A61B 8/481 600/424 |
| 2008/0171939 A1 | 7/2008 | Ishihara | |
| 2009/0105579 A1 | 4/2009 | Garibaldi | |
| 2009/0275834 A1 * | 11/2009 | Watanabe | A61B 8/463 600/443 |
| 2009/0306509 A1 | 12/2009 | Pedersen et al. | |
| 2010/0113930 A1 | 5/2010 | Miyachi | |
| 2010/0210946 A1 | 8/2010 | Harada et al. | |
| 2010/0240992 A1 * | 9/2010 | Hao | G01S 7/5205 600/437 |
| 2011/0257527 A1 | 10/2011 | Suri | |
| 2011/0299754 A1 | 12/2011 | Suri | |
| 2012/0078099 A1 | 3/2012 | Suri | |
| 2012/0179042 A1 | 7/2012 | Fukumoto et al. | |
| 2012/0296214 A1 | 11/2012 | Urabe et al. | |
| 2013/0046168 A1 | 2/2013 | Sui | |
| 2013/0218024 A1 * | 8/2013 | Boctor | A61B 5/0077 600/476 |
| 2013/0321262 A1 | 12/2013 | Scheter | |
| 2014/0066770 A1 | 3/2014 | Watanabe et al. | |
| 2014/0081142 A1 * | 3/2014 | Toma | A61B 8/4263 600/443 |
| 2014/0100440 A1 | 4/2014 | Cheline et al. | |
| 2014/0249417 A1 | 9/2014 | Ookouchi et al. | |
| 2014/0275986 A1 * | 9/2014 | Vertikov | A61B 5/0066 600/424 |
| 2014/0276059 A1 * | 9/2014 | Sheehan | A61B 8/12 600/443 |
| 2014/0276062 A1 | 9/2014 | Kondoh | |
| 2014/0303499 A1 | 10/2014 | Toma et al. | |
| 2014/0369583 A1 | 12/2014 | Toji et al. | |
| 2014/0371593 A1 | 12/2014 | Kondoh | |
| 2015/0009997 A1 | 1/2015 | Balassanian | |
| 2015/0025380 A1 | 1/2015 | Azegami et al. | |
| 2015/0055846 A1 | 2/2015 | Haque | |
| 2015/0099974 A1 | 4/2015 | Kelly et al. | |
| 2015/0209004 A1 | 7/2015 | Tamada | |
| 2015/0310581 A1 | 10/2015 | Radulescu et al. | |
| 2015/0359512 A1 | 12/2015 | Boctor et al. | |
| 2015/0359605 A1 | 12/2015 | O'Brien-Coon et al. | |
| 2016/0000408 A1 | 1/2016 | Matsunaga et al. | |
| 2016/0157814 A1 | 6/2016 | Palanisamy et al. | |
| 2016/0157826 A1 | 6/2016 | Sisodia et al. | |
| 2016/0331469 A1 | 11/2016 | Hall et al. | |
| 2016/0374562 A1 | 12/2016 | Vertikov | |
| 2017/0032995 A1 | 2/2017 | Cox | |
| 2017/0086785 A1 | 3/2017 | Bjaerum | |
| 2017/0090571 A1 | 3/2017 | Bjaerum et al. | |
| 2017/0265831 A1 * | 9/2017 | Sankaran | G16H 50/30 |
| 2017/0372475 A1 * | 12/2017 | Gulsun | G06N 3/02 |
| 2018/0014810 A1 | 1/2018 | Chen et al. | |
| 2018/0070915 A1 | 3/2018 | Miyachi | |
| 2018/0220991 A1 * | 8/2018 | O'Brien | A61B 8/488 |
| 2019/0015078 A1 | 1/2019 | Saad et al. | |
| 2019/0046153 A1 | 2/2019 | Tanaka et al. | |
| 2019/0239848 A1 | 8/2019 | Bedi et al. | |
| 2020/0151872 A1 * | 5/2020 | Ma | A61B 8/085 |

FOREIGN PATENT DOCUMENTS

| | | |
|---|---|---|
| EP | 1997436 B1 | 10/2014 |
| JP | 2008161220 | 7/2008 |
| KR | 20140103932 | 8/2014 |
| WO | 2013067419 A1 | 5/2013 |
| WO | 2019212992 | 11/2019 |

OTHER PUBLICATIONS

Akosha, et al., "Carotid ultrasound for risk clarification in young to middle-aged adults undergoing elective coronary angiography," Am J. Hypertens 19(12):1256-61, Dec. 2006.

Akosha, et al., "Pilot results of the Early Detection by Ultrasound of Carotid Artery Intima-Media Thickness Evaluation (EDUCATE) study," Am. J. Hypertens 20:1183-1188, Nov. 2007.

Camacho, et al., "Phase Coherence Imaging," IEEE Transactions on Ultrasonics, Ferroelectrics, and Frequency Control, vol. 56, No. 5, pp. 958-974, May 2009.

Canny, J., "A Computational Approach to Edge Detection," IEEE Trans. Pattern Anal. Mach. Intell., Jun. 1986;8(6):679-98.

Demi, et al., "The first order absolute moment in low-level image processing," in Proceedings of 13th International Conference on Digital Signal Processing, vol. 2, No. 1, pp. 511-514, 1997.

Drechsler, et al., "Hierarchical decomposition of vessel skeletons for graph creation and feature extraction," Proc.—2010 IEEE Int. Conf. on Bioinformatics and Biomedicine BIBM 2010, pp. 456-461, 2010.

Ibanez, et al., "Diagnosis of Atherosclerosis by Imaging," The American Journal of Medicine, vol. 122, Issue 1, Supplement, Jan. 2009, pp. S15-S25.

(56) References Cited

OTHER PUBLICATIONS

Illea, et al., "Fully Automated Segmentation and Tracking of the Intima Media Thickness in Ultrasound Video Sequences of the Common Carotid Artery," IEEE Trans. Ultrason. Ferroelectr. Freq. Control, vol. 60, No. 1, pp. 158-177, Jan. 2013.

Jespersen, et al., "Multi-Angle Compound Imaging," Ultrasonic Imaging, 20(2):81-102, May 1998.

Kaehler, et. al., "Learning OpenCV 3" Computer Vision in C++ with the OpenCV Library," O'Reilly Media, Inc., 2016.

Li, et al., "Adaptive Imaging Using the Generalized Coherence Factor," IEEE Transactions on Ultrasonics, Ferroelectrics and Frequency Control, vol. 50, No. 2, pp. 128-141, 2003.

Lorenz, et al., "A Guassian model approach for the prediction of speckle reduction with spatial and frequency compounding," Proceedings of the IEEE Ultrasonics Symposium 2:1097-1101 vol. 2, Dec. 1996.

Mitzev, et al., "Concatenated decision paths classification for datasets with small number of class labels," ICPRAM 2017, Porto, Portugal, Feb. 2017, pp. 410-417.

Molinari, et al., "A state of the art review on intima-media thickness (IMT) measurement and wall segmentation techniques for carotid ultrasound," Comput. Methods Programs Biomed., vol. 100, No. 3, pp. 201-221, 2010.

Neuschler, et al., "Diagnosis of Breast Masses Using Opto-Acoustics," American Roentgen Ray Society, MS Powerpoint Presentation, pp. 1-40.

Oraevsky, et al., "Optoacoustic Tomography," in Biomedical Photonics Handbook, ed. by T. VoDink, CRC Press, Boca Raton, Florida, vol. PM125, Chapter 34, pp. 34/1-34/34.

Otsu, N., "A Threshold Selection Method from Gray-Level Histograms," IEEE Trans. Sys. Man. Cyber, vol. SMC-9, No. 1, pp. 62-66, 1979.

Rossi, et al., "Automatic localization of intimal and adventitial carotid artery layers with noninvasive ultrasound: a novel of algorithm providing scan quality control," Ultrasound Med. Biol., vol. 36, No. 3, pp. 467-479, Mar. 2010.

Touboul, et al., "Mannheim Carotid Intima-Media Thickness Consensus (2004-2006)," Cardiovascular Diseases, vol. 23, pp. 75-80, 2007.

Best, S., "'The Future of Medical Scans? Nintendo Wi-inspired 7 Pound Microchip Turns 2D Ultrasound Machines into 3D Imaging Devices,'", DailyMail.com, Oct. 31, 2017, http://www.dailymail.co.uk/sciencetech/article-5035775/Microchip-turns-ultrasound-machines-3D-image-devices.html.

Hasegawa, H., et al., "Detection of lumen-intima interface of posterior wall for measurement of elasticity of the humad carotid artery", IEEE Transactions on Ultrasonic, Ferroelectrics, and Frequency Control, IEEE, USA, vol. 51, No. 1, pp. 93-108.

B-mode ultrasound common carotid artery intima-media thickness and external diameter: cross-sectional and longitudinal associations with carotid atherosclerosis in a large population sample (Eigenbrodt, M. L. et al.) Cardiovascular Ultrasound, vol. 6, Mar. 5, 2008.

International Searching Authority, International Search Report and Written Opinion of PCT/US2019/029739, mailed Jul. 8, 2019; 13 pages.

U.S. Appl. No. 62/627,457, filed Feb. 7, 2018.

International Searching Authority, International Search Report and Written Opinion of PCT/US2019/016663 mailed Apr. 24, 2019, 10 pages.

F. Faita et al, "Real-time Measurement System for Evaluation of the Carotid Intima-Media Thickness With a Robust Edge Operator", Journal of Ultrasound Medicine, vol. 27, p. 1353-1361, 2008.

F. Molinari et al, "Automated carotid IMT measurement and its validation in low contrast ultrasound database of patient indian population epidemiological study: results of AtheroEdge™ Software", Int'l Angiology, vol. 31, No. 1, pp. 1-22, Feb. 2012.

R. Menchon-Lara et al, "Automatic detection of the inti ma media thickness in ultrasound images of the common carotid artery using neural networks", Medicine & Biological Engineering & Computing, vol. 52, pp. 169-181, Nov. 2013.

R. Menchon-Lara et al, "Early-stage atherosclerosis detection using deep learning over carotid ultrasound images", Applied Soft Computing, vol. 49, pp. 616-628, Sep. 2016.

\* cited by examiner

Calculation Profile: CVD Risk

Estimation of 10 year Cardiovascular Disease Risk

Reference: Anderson et al. CCS Dyslipidemia Guidelines Update 2012.

Risk Factor | | Points
--- | --- | ---
Sex | Male | 
Age (30 - 75) | 33 | 0
Smoker | ○ Yes  ● No | 0
Diabetic | ○ Yes  ● No | 0
Blood Pressure | 543 / 345 mm Hg | 3
Blood Pressure is Treated | ☐ | 
Total Cholesterol | 0 mmol/L | 0
HDL Cholesterol | 0 mmol/L | 0

☐ Cardiovascular disease family history in first degree relatives before 55 for men or 65 for women.

Total Points  3
Risk of heart disease in 10 years  2.8%

[ OK ]  [ Close ]

*FIG. 31*

METHOD AND APPARATUS FOR THE AUTOMATIC DETECTION OF ATHEROMAS IN PERIPHERAL ARTERIES

CROSS-REFERENCE TO RELATED APPLICATION(S)

The present application is a continuation of International Application PCT/US2019/029739, filed Apr. 29, 2019, and claims the benefit of, and priority to, U.S. provisional patent application No. 62/664,616, filed Apr. 30, 2018, both of which are hereby incorporated by reference herein in their entireties and made part of the present disclosure.

TECHNICAL FIELD

This disclosed technology relates to an apparatus and method for the automatic detection of incipient atheroma in the asymptomatic population, which is important in preventative medicine. This disclosed technology focuses on the optimization, analysis, and calculations from ultrasound data to determine whether an asymptomatic individual should receive cholesterol lowering drugs or other medical therapies. Specifically, this disclosed technology refers to an apparatus and method which analyzes ultrasound data to enable medical care givers who are not trained ultrasound specialists as well as primary care physicians to detect the presence of atherosclerosis so they can better target individuals who would benefit from preventive medical interventions. Spatially and temporally registered ultrasound data of peripheral arteries are used to segment the artery in each transverse plane, identify the optimal acquisition angle, combine the necessary acquisition angles for optimal wall-lumen contrast, assess the intima-media thickness (IMT) in each slice, calculate the intima-media area (IMA) in each slice, combine the slices together for intima-media volume (IMV) calculation, and recommend whether sufficient evidence exists to start preventative medical treatment.

BACKGROUND

Diagnostic ultrasound is routinely used in hospital settings worldwide. However, its core advantages of non-ionizing radiation, low cost and portability are not exploited in the much larger and more frequently utilized primary care market. While perceived impediments of size, weight and cost have been addressed by incumbent developers, the real impediment to widespread adoption in a primary care setting is the prohibitive overhead cost of acquisition expertise by a sonographer and interpretation aptitude by a radiologist or cardiologist. The disclosed technology aims to remedy this hurdle by focusing on a specific disease that affects a significant percentage of the population and by automating many of the steps for data acquisition, optimization and interpretation.

The disclosed technology targets the detection of subclinical atherosclerotic cardiovascular disease (ASCVD), which is a chronic disorder developing insidiously throughout life and eventually manifesting itself into catastrophic symptoms of myocardial infarction and ischemic stroke. Per the World Health Organization (WHO), 17.5 million people worldwide and 800,000 in the USA died from cardiovascular diseases in 2005; with the worldwide number expected to increase to almost 25 million by 2020. Most of these deaths could be prevented or delayed through judicious choice of lifestyle modifications and initiation of lipid lowering therapy. The decision to offer medical intervention to select individuals based solely on risk factor assessment such as cholesterol level or family history is not adequate.

This disclosed technology aims to provide physicians with direct evidence of the progression to arterial damage from ASCVD risk factors, so they more aggressively target such individuals with lipid lowering therapy.

As mentioned earlier, a key component to increase the adoption of ultrasound techniques in the primary care physician's office is simplification of the apparatus and methods used to successfully acquire and analyze ultrasound data of peripheral arteries such as the extracranial carotid, brachial, iliac, and femoral arteries. The acquired ultrasound data which are temporally and spatially registered are then automatically analyzed to determine the patient's suitability for medical intervention. This disclosed technology describes an apparatus and method that are used to calculate optimal image acquisition parameters (e.g., automatic image acquisition optimization) to effectively identify optimal ultrasound images and automatically interpret the ultrasound images for pathological findings to guide treatment methods.

U.S. Patent Application No. 62/627,457 titled, "Apparatus and Method to Guide Ultrasound Acquisition of the Peripheral Arteries in the Transverse Plane" ("the '457 application), which is hereby incorporated by reference in its entirety herein, focuses on guiding a technician, medical assistant or primary care physician during the ultrasound acquisition of the three-dimensional data. In some embodiments of the apparatus disclosed in the '457 application, the major components are tissue equalization, carotid tagging, transverse plane guidance, data recording and data quality confirmation.

BRIEF DESCRIPTION OF THE DRAWINGS

FIGS. 2a and 2b illustrate examples from a training dataset used to train a supervised algorithm for vessel of interest detection, wherein FIG. 2a illustrates examples of "no vessel of interest" class labels and FIG. 2b illustrates examples of "vessel of interest" class labels.

FIG. 8a illustrates the carotid insonified by one imaging angle. FIG. 8b illustrates how, as the carotid turns downward, the specular behavior of the reflection prevents the imaging apparatus from showing clear visibility in lateral regions of the carotid. FIG. 8c illustrates how, if multiple visualization angles are used, then carotid perimeter is visualized with optimal brightness and contrast to the lumen.

FIG. 14a illustrates automatic VOI detection using normalized correlation of B-mode RF data and sparse CFM image, FIG. 14b illustrates automatic VOI detection using CFM and B-mode images, and FIG. 14c illustrates automatic VOI detection using correlation of RF frames and B-mode data.

FIG. 19 also diagrams the echo amplitude between the multiple layers, lumen and tissue with the origin at the lumen center.

FIG. 23 shows the amplitude of the data as a B-mode image. The horizontal axis corresponds to radial direction with the center of the vessel being on the left. The right sub-figure of FIG. 23 shows the amplitude of the signal along a single line.

FIG. 29a illustrates a three-dimensional rendered graph to show the measurements or the differences. FIG. 29b illustrates a contour graph where the axes are the longitudinal and angular positions and the contours shows the measurements or difference between the media-adventitia and lumen-intima. FIG. 29c illustrate a colormap (in grayscale) where the axes are the longitudinal and angular positions and the contours shows the measurements or difference between the media-adventitia and lumen-intima. FIG. 29d illustrates a max IMT graph where the axes are the longitudinal and angular positions and the contours shows the measurements or difference between the media-adventitia and lumen-intima. FIG. 29e illustrates the IMA graphed as a function of longitudinal position.

FIG. 31 illustrates an embodiment of an analysis tool incorporating traditional risk factors (TRFs).

DETAILED DESCRIPTION

Figure 1A:
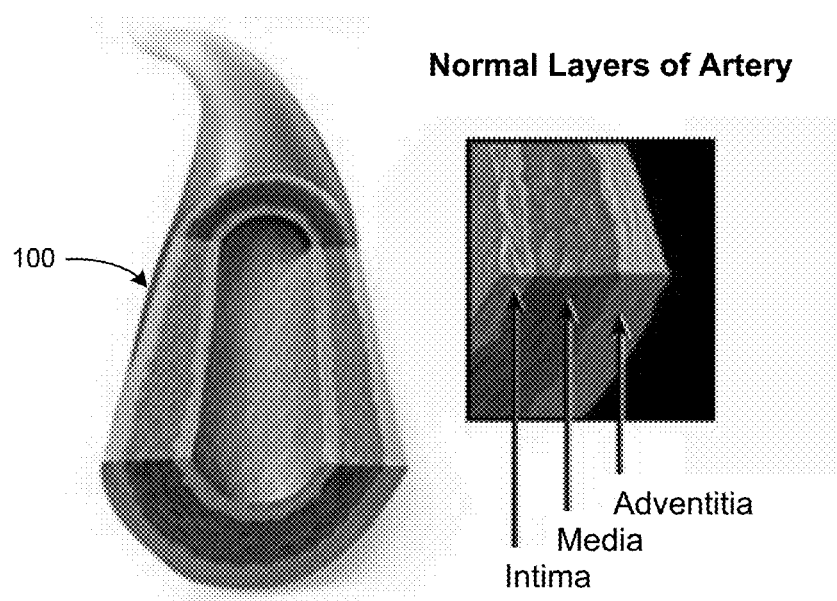
FIGS. 1a and 1b illustrate a normal artery cross section and an artery with atheroma

The extracranial carotid, iliac, femoral, and brachial arteries are key vascular areas where physicians look for the development of potential atherosclerotic plaques since disease found in these regions suggest atherosclerotic plaques may be forming in other arteries. Although the following description focuses on the carotid, it is important to note that these same techniques apply to other peripheral arteries such as the femoral.

The data produced in the manner described in the '457 application will be made-up of multiple temporally and spatially registered signals of ultrasound backscatter of tissue. In some cases, the data will include backscatter from the same tissue region in the volume of interest. In some embodiments, the apparatus data has distinct steering angles which may be one, two, three, or multiple steering angles, which are combined to optimize the brightness of the wall and the darkness of the lumen. In another embodiment, the apparatus produces a virtual aperture by controlling the transmit and receive foci to optimize the vessel wall contrast with the lumen. In yet another embodiment, the apparatus combines data of multiple data sets from the same tissue region or adjacent tissue regions to improve the SNR and measurement. In yet another embodiment, the apparatus maps multiple data characteristics to a goodness factor which selectively combines specific regions of two different data sets. The goodness factor may include transducer plane orthogonality to the vessel longitudinal axis, wall contrast, focal position, transducer aperture position relative to vessel position. The goodness factor is typically a mapped variable of many other variables where the error is a minimum. For example, the square root of the sum of the squares where the square is the difference between ideal or accepted value to the actual value.

Since the goal is to determine whether an atheroma is present, it is not necessary for the apparatus to develop merged images (e.g. compounding) with uniform brightness or acceptable readability by a radiologist as is the case with a conventional ultrasound imaging system. In the present inventions, it is not required that images be presented to the operator. However, different acquisition angles of the ultrasound backscatter are still an advantage. In some embodiments, ultrasound backscatter at optimal acquisition angles is used to select the radio-frequency ("RF") data sets for each transverse plane. This is later combined for analysis that focuses on wall segmentation and post-processing with spatial filters or interpolation. The artery is segmented along the adventitia to determine the optimal acquisition angle, which maximizes the contrast between the lumen and vessel wall. Each acquisition angle is identified as being applicable to a specific distance and angle along the arterial wall. Transformations are applied to more readily calculate IMT for each acquisition angle and thus the entire IMT for the slice. The individual slice measurements are combined with additional filters to create an intima-media volume (IMV) map that is used to determine whether an atheroma is present (i.e., anatomical measurements are automatically interpreted to determine whether an atheroma is present).

Atherosys (the assignee of the present application at the time of filing) is developing a device to be used in a primary care office to guide the decision for prophylactic medical intervention, by (1) detecting the presence of atheromas in arteries and combining this information with traditional risk factor scoring (2) providing a volumetric index of atheroma burden in arteries to allow the user to monitor therapy effectiveness in follow-up examinations. The preferred embodiment of the device does not display an ultrasound image but uses spatially and temporally registered ultrasound data acquired with the transducer approximately orthogonal to the artery longitudinal axis. Typically, conventional ultrasound scanners present images to the user which enables the user to perform measurements on the data and relies on user expertise to interpret the images. Unlike conventional ultrasound scanners, the ultrasound apparatus disclosed herein guides the user during data acquisition (see commonly owned '457 application), and performs all the necessary steps to interpret the data to yield a simple yes/no answer to whether the subject should be targeted for medical intervention. Steps for determining a yes/no answer can include: (1) guiding the user to acquire data ('457 application); (2) detecting vessels; (3) identifying artery of interest from the detected vessels; (4) detecting the presence of atheromas in the artery of interest where the detection of atheromas follows the generally accepted criteria for atheromas; (5) combining atheroma information with traditional risk factor scoring to determine whether an individual should be targeted for therapy; and (6) providing an easy to read index of atheroma burden based on volumetric data to allow the user to assess therapy effectiveness in follow-up examinations. It is important to note that in this preferred embodiment, the device can complete the required tasks without requiring the presentation of ultrasound images to the apparatus operator.

The follow-up inspection of the treatment efficacy is not generally reliable by comparing the state of each individual atheroma, as the data acquisition is performed at different time instances (days, weeks, months). A more reliable marker for efficacy (effectiveness) of the treatment is to measure the change in the total atheroma burden. This method is robust as it does not require spatial alignment (registration) of volume data from different scans, but only the identification of the regions where atheromas were detected. It only requires that the same or substantially the same portion of the artery is scanned at every exam. So, in addition to the detection of the presence of atheromas, the device calculates the vessel wall volume as well as the total luminal volume.

The device disclosed herein guides the user in the acquisition of the same portion of the vessel by detecting landmarks for a vessel. In the case of extracranial carotid and iliofemoral artery, a unique anatomic marker is the bifurcation. The bifurcation is detected by finding the center lines of the common and the resultant bifurcated arteries. This junction registers the coordinate systems of the two different acquisitions, which enables accurate treatment assessment or if treatment was not recommended, any changes in the vessel wall volume or total luminal volume.

The above-referenced pending patent application targets the acquisition and guidance aspects of the device (USPTO 62/627,457). The current application discloses an apparatus for data analysis which guides the decision of initial therapy and follow-up examinations for assessing therapy effectiveness.

Figure 1B:
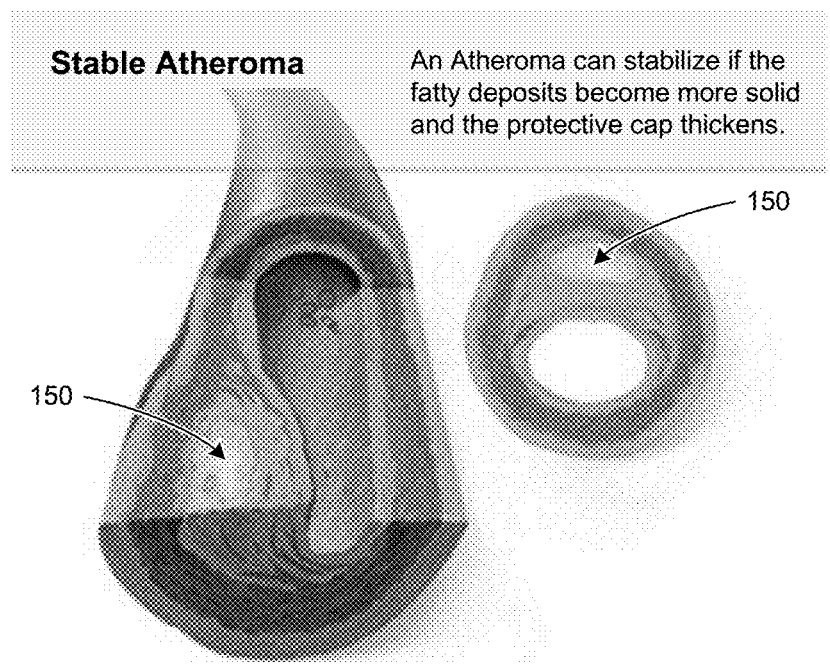

FIG. 1a shows a three-dimensional (3D) sketch of a healthy artery wall 100, which consists of adventitia, media, and intima. A key measurement that determines arterial health is the intimal-media thickness (IMT) as explained in Touboul, P. J., et. al., "Mannheim Carotid Intima-Media Thickness Consensus (2004-2006)", Cardiovascular Diseases, vol. 23, pp. 75-80, 2007, the entirety of which is hereby incorporated by reference and made part of the present disclosure. This article states that atherosclerosis is to be defined "as intima media thickness >1.50 mm". This definition has subsequently been adopted by various international scientific bodies (see, e.g., ASE Consensus Statement, Journal of the American Society of Echocardiography, 2008; 21(2): 93-111; the ACC/AHA Guidelines, Journal of the American College of Cardiology, 2010; 56(25): e50-103; the ESC Guidelines, European Heart Journal, 2012; 33: 1635-1701; and Canadian Guidelines, Canadian Journal of Cardiology 2013; 29: 151-167, the entirety of which are hereby incorporated by reference and made part of the present disclosure). FIG. 1b shows a case where an atheromatous plaque 150 has started to build up in the arterial wall, which creates less optimal flow. To improve the detection of atheroma, IMT is preferably determined from cross-sectional ultrasound images of the artery.

The '457 application referenced above describes an apparatus and methods to keep the carotid in the middle of the ultrasound image when using a linear array. This enables an optimization of contrast and spatial resolution around the carotid which enhances the accuracy of IMT automated measurements.

As will be described in further detail below, the disclosed technology is an apparatus that automatically collects and analyzes (e.g., interprets) ultrasound data to determine whether an atheroma is present (e.g., by anatomical measurements) in a patients artery and in some embodiments, whether it is recommended to treat the patient with lipid-lowering or other therapies. The apparatus directs an operator to obtain ultrasound data along a length of a vessel with a probe position that is nearly orthogonal to the lumen of the vessel. The received ultrasound data are then processed to automatically identify vessels (e.g., arteries and veins) in the image from which an artery of interest is identified. Echo data representing reflections from the constituent layers of the identified artery of interest are then further optimized. From the processed echo data, the IMT, IMA and IMV measurements are made and presented to the operator.

As described in the '457 application, echo data are received by a processor within the ultrasound apparatus to determine if the echo data are representative of moving blood flow in the field of view and if the imaging probe is oriented in a direction that is nearly orthogonal to the vessel flow. A user interface (e.g. lights or other markings) on the ultrasound probe are controlled by the disclosed apparatus to alert the user how the probe should be oriented to obtain strong reflections from the vessel walls. Echo data from the vessel are obtained as the user moves the probe along a length of the vessel and stored in a memory of the ultrasound apparatus. As will be described in detail below, once the data are stored, the data are analyzed by a processor (CPU, DSP, GPU or the like or a combination thereof) in the ultrasound apparatus to detect and measure an atheroma if present.

This following disclosure describes various methods used by a processor to obtain and analyze the echo data (e.g., digital echo data converted from return echo signals by processing electronics) and is separated into multiple sections which typically occur sequentially:
i. Automated or semi-automated acquisition of ultrasound data which contains the vessel of interest (e.g. carotid)
ii. Automated artery of interest identification (e.g. carotid)
iii. Automatic extraction of the volume of interest based on confirmation that the vessel of interest is contained therein
iv. Automated ultrasound data optimization to enhance arterial wall contrast for optimal IMT and IMV measurements
v. Ultrasound image transformations to automate IMT and IMV measurements
vi. Methods to report study findings Each step listed is part of getting the best prediction of IMV and determining whether the patient has an atheroma, Next, the physician determines whether to initiate lipid lowering therapy.

Automatic Artery Identification

Although the following description focuses on the carotid, it is important to note that these same techniques apply to other vessels such as the femoral artery. The common carotid, carotid bifurcation, and internal and external carotids are identified while the volume data is being acquired or after the volume of interest has been acquired. In some embodiments, ultrasound data are captured by the apparatus and processed after the data are stored in apparatus memory to identify an artery of interest. In other embodiments, the data are analyzed in real time as the data are being acquired. If carotid identification is done while the volume data are acquired, then feedback is given to the operator to guide either the manual movement of the transducer to follow the carotid or to inform the operator that the carotid was successfully captured. Automatic vessel identification is done through machine learning techniques or other deterministic methods, Machine Learning Machine learning uses self-derived features and standard features of the carotid that are used to train the disclosed apparatus to automatically identify an artery. The accuracy of the disclosed apparatus using machine learning improves through data set training. Some of the features that are used include (i) Carotid wall brightness (ii) Carotid wall elastic properties (iii) Carotid wall pulsatility (iv) Common carotid cross-sectional diameter (v) Carotid location in spatially registered data sets (vi) Flow data (vii) Correlation of RF data showing speckle decorrelation (viii) Bifurcation (ix) Bulb.

Machine Learning: Training

Figure 2A:
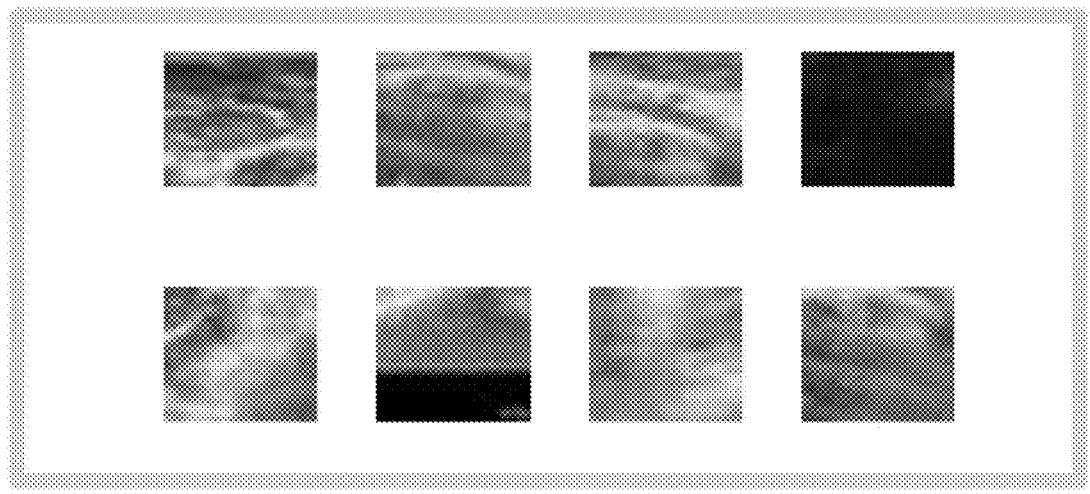
Figure 2B:
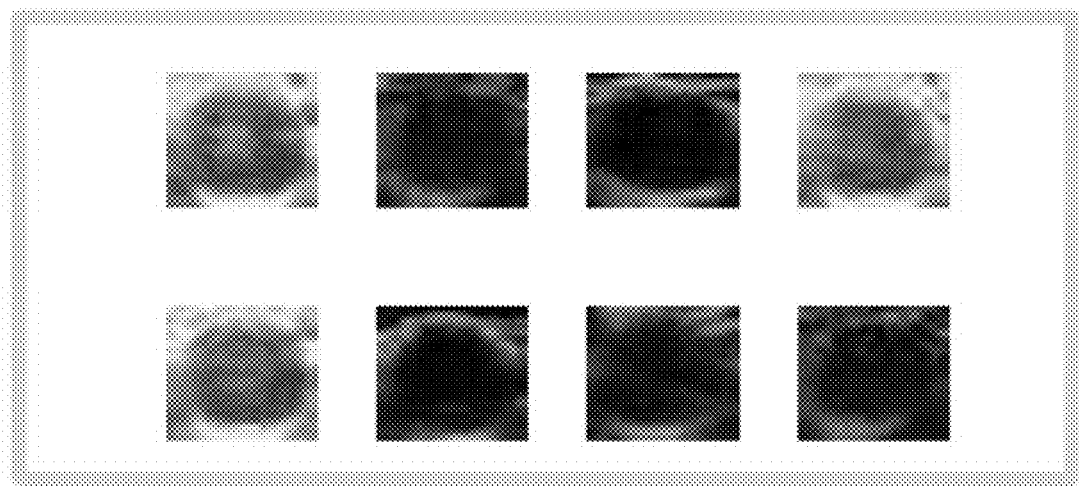

A training dataset is constructed by manually defining and cropping images of the "vessel of interest" and "no vessel of interest" areas from the original ultrasound images. FIGS. 2a and 2b show several such examples of "no vessel of interest" areas 200 and "vessel of interest" areas 202, respectively. In this case, the backscatter data are used to generate an ultrasound image. All the training images are resized to one standard size and then used for training.

In this example, the cropped images are converted into time series or vector by unwrapping the row-column data. The conversion is done by simply iterating through the rows of the image matrix and storing the pixels' gray values in a vector as shown on FIG. 3.

The constructed time series vector is pre-processed by normalizing it as shown in Equation (1).

$$X=(X-\mu)/\sigma \quad (1)$$

After normalizing, the time series is compressed by averaging every four samples. That shortens the time series, which reduces the training time without losing accuracy.

A supervised machine learning algorithm is used such as the Concatenated Decision Path (CDP) algorithm, which is described in I. Mitzev, N. Younan. 2017. "Concatenated decision paths classification for datasets with small number of class labels." ICPRAM. Porto, Portugal, the entirety of which is incorporated by reference and made part of the present disclosure, because of its simplicity and short training time. The CDP algorithm requires definition of the number of decision trees, which for the current case is set to 200. The parameters of training are saved and used for further automatic recognition.

Figure 3:
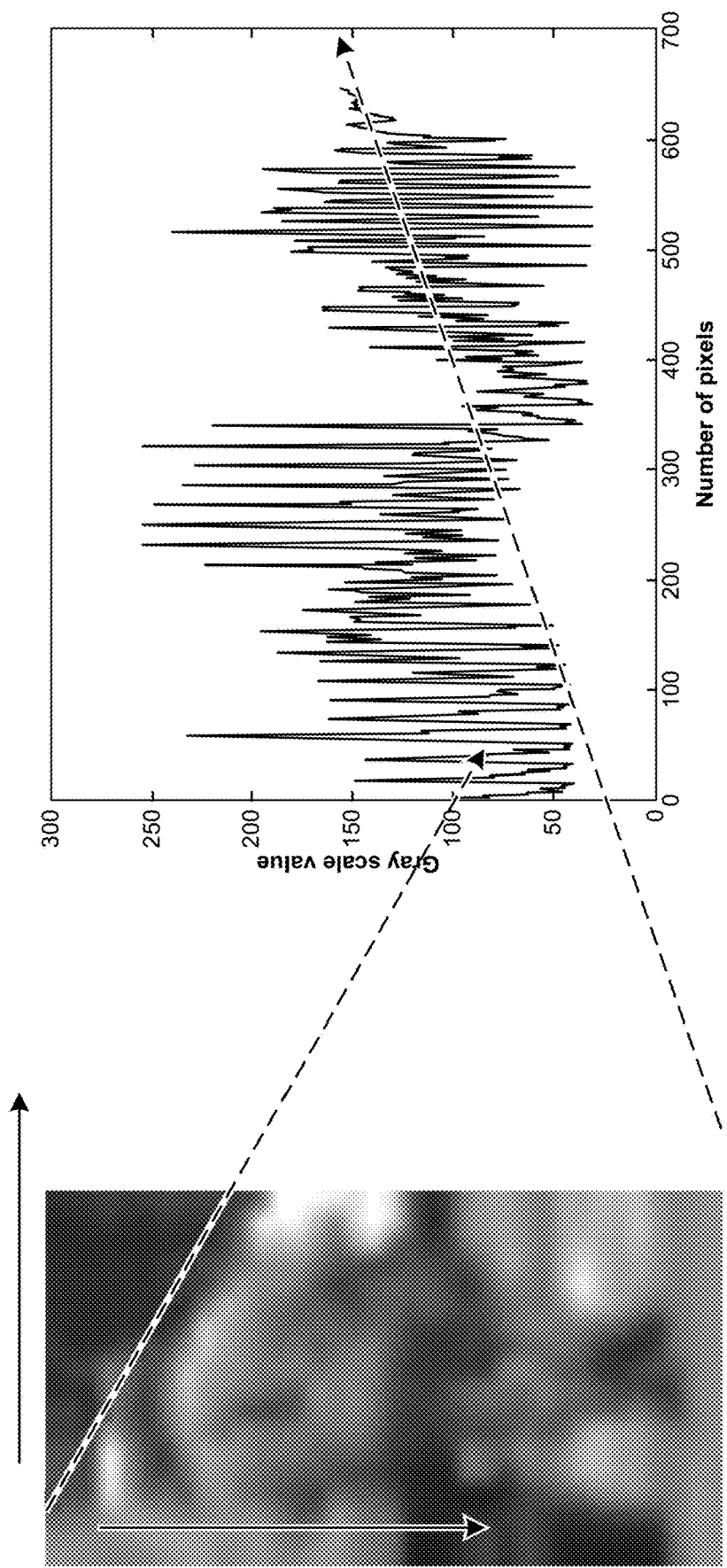
FIG. 3 is an illustration of converting an image into time series by iterating through rows of the image matrix.

FIG. 3 is an illustration of converting an image 300 into time series 302 by iterating through rows of the image matrix.

Machine Learning: Artery Identification

To analyze a new image, a sliding window is defined with a size equal to the size of the training images. As will be appreciated, the term "image" as used herein need not refer to a depiction of tissue that is shown to a user. An image refers to a spatially arranged collection of echo data that originates from the tissue that may or may not be shown to a user. An image may be pre- or post-scan converted echo data or may be a spatially arranged collection of RF echo data. This window slides across the investigated image horizontally with a specific step size and once it reaches the image vertical borders, it moves down the image also with a specific step size. On every step, the image that is surrounded by the moving window is classified as "vessel of interest" or "no vessel of interest" from the previously trained CDP algorithm. This method permits more than one possible "vessel of interest" per assessed image to be found. In some embodiments, the apparatus identifies the bifurcation of the artery since this has been part of the machine learning training set. Since the classification may find more than one "vessel of interest" per assessed image, there is an additional algorithm that eliminates falsely detected "vessels of interest" or "vessels of interest" that are redundant since they are from the same artery. This algorithm uses the probability and confidence intervals of the detected "vessels of interest" and removes others based on setting of a specific threshold.

It is important to note that once the anatomy (e.g. vessel) of a patient has been identified using the algorithm, it is possible for this data to become part of the training data sets. In some embodiments, the apparatus compares past scans to current scans to determine if arterial conditions have changed. This also increases the probability and improves the confidence interval of proper carotid detection.

Deterministic Methods

Deterministic Methods: New Patient

Figure 4:
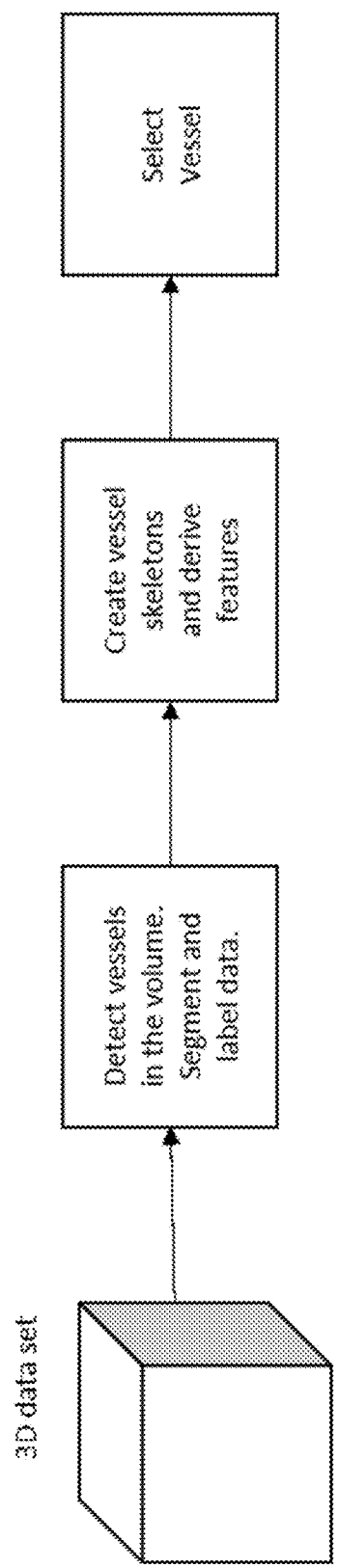
FIG. 4 illustrates a process flow used to identify the carotid through tests which are weighted differently and at distinct stages.

Machine learning leverages information of multiple data sets to train the apparatus to identify the carotid, Instead of using machine learning, another method is to use deterministic methods to identify the carotid that do not require the use of multiple data sets for training but use known anatomical attributes of the carotid. A process flow 400 is used to identify the carotid through tests which are weighted differently and at distinct stages (FIG. 4). In some embodiments, the first series of tests determine where the vessels are by analyzing color flow data or through RF correlation techniques combined with a noise model. FIG. 4 shows a 3D data set 402 where the first stage or block 404 correlates RF data acquired at a minimum of two different time intervals. If multiple 3D data sets which are temporally registered are analyzed, then this is defined as 4D data sets. Since the data set contains volume information, these two time points are at the same spatial location or at adjacent spatial locations. The relative intensity of scattered signal, the noise model, and signal correlation between the two time points or adjacent locations enable lumen or non-lumen identification. Since this is a 4D data set, lumens which are contiguous are identified throughout the volume. In this embodiment, after the vessels are identified in block 404, the next tests are used to find the carotid. Vessel skeletons are created in block 406 and features are derived for each contiguous lumen (see, e.g., K. Drechsler and C. O. Laura, "Hierarchical decomposition of vessel skeletons for graph creation and feature extraction," Proc.—2010 IEEE Int. Conf. Bioinforma. Biomed. BIBM 2010, pp. 456-461, 2010, the entire disclosure of which is incorporated by reference herein in its entirety). Lumens that combine into one vessel at a junction point are located along with length and average diameter of each vessel branch. The carotid is correctly located and selected in block 408—through one or more of the following features: (1) pulsatility to classify arteries versus veins (2) elastic properties of the vessel wall to distinguish arteries from veins (3) vessels that have diameters and depth within a specific range (4) the vessel that has the expected bifurcation and bulb which are contiguous with other parts of the vessel. Since the scanning direction is from the clavicular notch towards the head, the direction of bifurcation and bulb is known. Similar principles are applied to automatically detect other peripheral vessels of interest such as the femoral artery.

FIG. 4. Pipeline for the detection of the vessel of interest.

Deterministic Methods: New Patient—Detection of Voxels that Belong to a Vessel.

Figure 5:
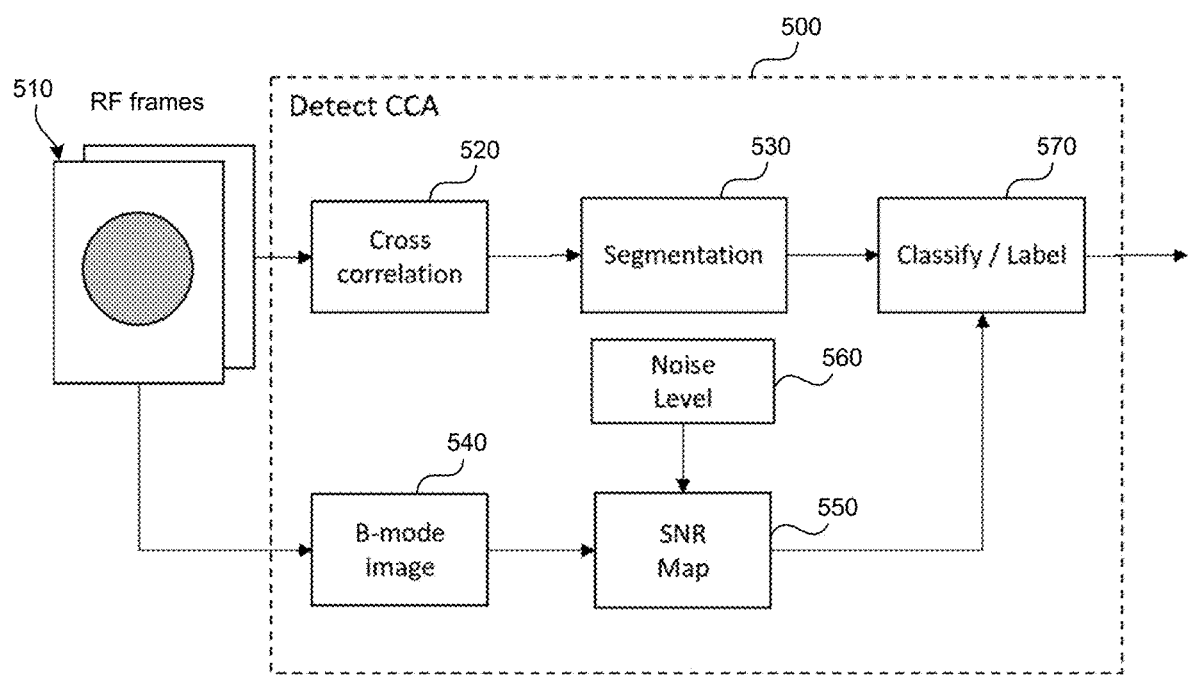
FIG. 5 illustrates a block diagram of a sub-system that detects the vessels in RF volumetric data.

FIG. 5 shows a block diagram of a sub-system 500 that detects the vessels in RF volumetric data. A sequence of RF frames 510 (2 or more) are fed in a block implemented by a processor that estimates a normalized cross-correlation 520 from each frame. The cross-correlation map is segmented. The segmentation threshold is chosen 530 based on the a priori knowledge about correlation of blood. The RF frames are also fed to a module 540 that generates B-mode images. The pixel level of the B-mode image is used to create a map of the signal-to-noise ratio (SNR Map) 550. The map level of the (thermal) noise is tabulated 560 per setup during the production of the device. The SNR Map and the segmented cross-correlation are then fed to a block 570 that labels the regions in the image.

Based on the typical values for the velocities in the common carotid artery, and the profile of the beam in the elevation direction, it is possible to pre-compute expected correlation values for the flow in an artery. An example for the common carotid artery is illustrated FIG. 6. It shows the correlation value between the signals from sequential frames as a function of radial distance from the center of the vessel. The correlation is shown for peak systolic and end diastolic velocities. The frame rate is set to 78 Hz. The peak systolic velocity is 48 cm/sec, and the peak end-diastolic velocity is 19 cm/sec. The flow profile is parabolic and is zero at the vessel wall. The flow is in a plane transverse to the imaging plane. The vessel has a circular or substantially circular cross-section.

Figure 6:
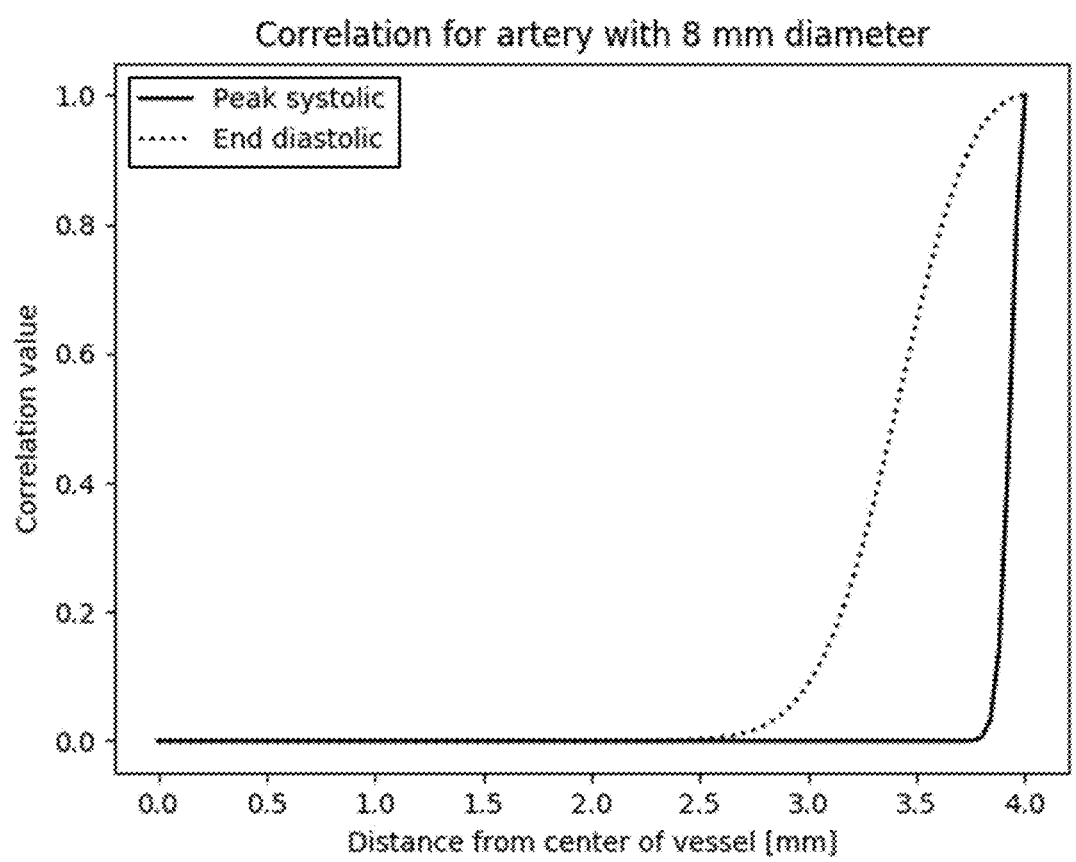
FIG. 6 illustrates a correlation value between the signals from sequential frames as a function of radial distance. The correlation is shown for peak systolic and end diastolic velocities. The frame rate is 78 Hz. The peak systolic velocity is 48 cm/sec and the peak end-diastolic velocity is 19 cm/sec. The flow profile is parabolic and is zero at the vessel wall. The flow is in a plane transverse to the imaging plane.

FIG. 6 illustrates correlation value between the signals from sequential frames as a function of radial distance from the center of the vessel for the common carotid artery.

Because the blood is moving in the carotid artery, the cross-correlation for areas of moving blood is expected to be low. The processor analyses the data frames and selects areas of low cross-correlation as likely representing a central area within a vessel. This example shows that if the threshold for the normalized cross-correlation for a voxel is set to be in the range between 0.1 and 0.2, then the voxels in most of the lumen will be detected for the arteries both in systole and diastole.

Deterministic Methods: New Patient—Detection of Voxels that Belong to a Vessel—Calculation of Vessel Parameters The segmented data are then subjected to an iterative thinning operation until the center line of the vessel is identified. Then the voxels of the center line are labelled as end, regular and branch voxels (see, e.g., K. Drechsler and C. O. Laura, "Hierarchical decomposition of vessel skeletons for graph creation and feature extraction," Proc.—2010 IEEE Int. Conf. Bioinforma. Biomed. BIBM 2010, pp. 456-461, 2010).

Assuming that $\vec{x}_n$ is the position of the center of voxel n from the center line of vessel, it is possible to calculate the length of each branch of the vessel as the sum of the distances between the centers of neighboring voxels that form the center line of the vessel:

$$\text{Length} = \sum_{n=1}^{N-1} \|\vec{x}_n - \vec{x}_{n+1}\|$$

where N is the number of voxels that belong to the center line of a given branch.

The volume of a vessel branch is calculated by summing the volumes of all the voxels that belong to the vessel branch.

The average diameter of a vessel branch is calculated as:

$$\text{Diameter} = \frac{2}{\sqrt{\pi}} \cdot \sqrt{\frac{\text{Volume}}{\text{Length}}}$$

Deterministic Methods: New Patient—Detection of Voxels that Belong to a Vessel—Vessel Selection The artery of interest is thereby detected based on the expected features of the artery:
1. Is bifurcation present. The skeleton of the vessel contains a branching voxel.
2. The diameter of the expected common part of the artery is within certain limits for the scanned vessel.
3. The lengths of the individual segments match the expected length for a successful scan. For the carotid artery, the device expects 3 cm common carotid artery and 2 cm for the inner and outer carotid arteries.

Deterministic Methods: New Patient—Detection of Voxels that Belong to a Vessel—Vessel Confirmation Once the carotid is confirmed in one frame, correlation methods between frames (e.g., 2D planes) are used to track the carotid through the entire 3D data. It is expected that this method confirms the same vessel of interest as the carotid regardless of which plane is used as the initial frame for detection. A matrix of all frames would show whether the vessel of interest identified by the detection algorithm is the same vessel of interest confirmed through correlation. Ideally, such a matrix would appear as illustrated in Table 1. However, in some cases the detected carotid within a frame may not match with the vessel of interest identified from frame-to-frame cross correlation which originated from the detected vessel of interest in another frame. This information is used to determine the confidence in the identified vessel of interest and assess the quality of the data.

In Table 1 (see below) multiple frames are listed in the rows and columns. In the rows, the vessel of interest is identified through detection means as listed above (deterministic or machine learning) and the vessels in the corresponding frames are determined through cross-correlation techniques. If the same vessel is identified through cross-correlation techniques as was either machine learning or deterministic methods, then the word 'same' is placed in the cell. If the vessel is different, then a flag may be thrown, and the quality of the data may be lowered. This method is also used to confirm the extent of the vessel wall.

If a previous analysis exists, then the recently recorded data set may be compared to a previously recorded data set for additional confidence that the carotid was selected. In fact, a previously recorded data set may be able to eliminate some of the steps to detect the carotid through a relative comparison with a previously recorded data set. It is important to note that the start of the bifurcation is a landmark feature that is used to register two or multiple acquisitions acquired at separate times. The bifurcation acts like a key so actual longitudinal locations along the carotid are accurately compared. This is especially important to track the effectiveness of therapy over time.

Deterministic Methods: Existing Patient

In the case of an existing patient, correct identification of the carotid may be accomplished with other or additional means. In some embodiments, the previous data set is compared with newly acquired data set to identify correct vessel. Features are used such as the bifurcation or bulb or a combination thereof to locate the common carotid, and internal and external carotids.

Arterial Wall to Lumen Resolution and Contrast Enhancements

The acquisition of the volume of interest containing the carotid has already been completed. Machine learning and/or deterministic methods have ensured that the right part of the vessel of interest has been acquired. This rough assessment of the volume of interest includes 3 cm of the common artery and 2 cm of the bifurcation and bulb. However, the data set includes redundant data and is not optimized to emphasize the contrast between the wall and lumen.

The acquisition includes already processed ultrasound backscatter vectors (e.g. detected data), focused RF data, or individual element RF data. In some embodiments, the apparatus uses the acquired data along with the carotid identification to further improve the resolution and contrast of the lumen to the arterial wall. Unlike conventional ultrasound imaging where imaging parameters are selected to produce a uniform image, the disclosed technology optimizes (e.g., dynamically optimizes) the imaging parameters so that measurements can be taken from the entire area of the identified vessel. The recorded a data (e.g., return echo data) that is stored in memory includes one or more transmit foci, one or more receive foci (e.g. dynamic focusing), one or more transducer acquisition angles, one or more transducer spatial positions interrogating the same carotid region, one or more multiple fields-of-view (FOV), one or more transmit apertures, one or more receive apertures. Given that the volume measurement is based on the disclosed apparatus' ability to detect the intima-media and media-adventitia boundaries, the measurement is improved through imaging parameter selection which optimizes the resolution and contrast of the vessel.

Acquisition Parameter Optimization

In the previous section, the carotid lumen and possibly part of the wall are identified. In some embodiments, the apparatus automatically tracks the lumen center to enable selection of ideal recorded data. Based on the position of the lumen center, the apparatus automatically selects the data

TABLE 1

Matrix confirming the same carotid vessel of interest has been identified across the entire volume data set.

| | | ROI IDENTIFIED THROUGH FRAME-TO-FRAME CROSS CORRELATION | | | | | | | |
|---|---|---|---|---|---|---|---|---|---|
| | | FR1 | FR2 | FR3 | FR4 | — | — | — | FRN |
| ROI IDENTIFIED THROUGH DETECTION | FR1 | ✗ | Same | Same | Same | — | — | — | Same |
| | FR2 | Same | ✗ | Same | Same | — | — | — | Same |
| | FR3 | Same | Same | ✗ | Same | — | — | — | Same |
| | FR4 | Same | Same | — | ✗ | — | — | — | Same |
| | — | — | — | — | — | ✗ | — | — | Same |
| | — | — | — | — | — | — | ✗ | — | Same |
| | — | — | — | — | — | — | — | ✗ | — |
| | FRN | Same | Same | Same | Same | Same | Same | Same | ✗ | obtained with an ideal transmit focus based on the depth of the detected lumen center. In some embodiments, multiple transmit foci are selected dependent (e.g., dynamically) on the vessel diameter and the depth-of-field (DOF) of the recorded transmit foci. Similarly, multiple receive foci are selected (e.g., dynamically) also dependent on the vessel diameter and DOF of the recorded receive signal. In the same embodiment or another embodiment, the disclosed apparatus automatically/dynamically selects the transmit aperture size to optimize the lateral resolution of the ultrasound vector at the lumen center and at the vessel wall. Similarly, the apparatus automatically/dynamically selects the receive aperture size to optimize the lateral resolution of the ultrasound vector. In yet another embodiment, the apparatus optimizes the number of transmit and receive vectors necessary for the analysis through vector selection which interrogates the lumen and carotid wall. Similarly, the disclosed apparatus optimizes the ultrasound FOV by only including data which includes the vessel of interest.

Data Set Optimization

It is expected that the recorded data includes redundant interrogations of the same vessel regions. The previously described techniques identify the carotid within the volume of interest. In some embodiments, the direction (orientation) of the vessel longitudinal axis is determined at each lumen location. This direction is compared to the recorded transducer position for each backscatter data. Next, the apparatus calculates the angle that the acquisition plane makes to the vessel longitudinal axis. In some embodiments, the angle is determined based a trigonometric analysis of the "ovalness" of a detected vessel lumen. Data acquisitions where the vessel longitudinal direction is the closest to the normal of the transducer plane are selected for the possible measurement. The apparatus completes this exercise for the acquired data such that a sufficient number of transducer positions are selected to image the entire volume of interest.

Once the data set is optimized by automatically analyzing the angle between the transducer acquisition plane to vessel longitudinal axis, other acquisition parameters are used to further optimize the volume data set. In some embodiments, the apparatus generates the optimal volume data set from the common carotid near the clavicular notch to slightly beyond the bifurcation by analyzing multiple images of the same VOI and selecting the best data to generate the final image. Underperforming data in key areas such as wall-to-lumen contrast and poor centering of the carotid to the transducer aperture are discarded.

Ratio of the lumen brightness to wall brightness is typically ideal when the transducer acquisition plane is normal to the vessel wall. Automatic ultrasound data analysis keeps the data that has the highest wall-to-lumen contrast such that the entire vessel volume is obtained for an entire cardiac cycle at multiple acquisition angles. In another embodiment, ultrasound data that have lower contrast between the lumen and wall when other data exist are discarded.

Poor centering of carotid to transducer aperture: The closer the vessel is to the center of the acquisition aperture, the more acquisition choices are available to optimize the wall-to-lumen contrast around the entire vessel. Similarly, ultrasound data where the vessel is not well centered relative to the transducer aperture when other data exist with better centering are discarded.

Estimate of incidence angle to wall slope: In the transverse plane, the carotid is best described as an ellipse. The acquisition angle which optimizes wall-to-lumen contrast is normal to the vessel wall which can be chosen for the entire vessel using optimal angle extrapolation from the initial acquisition angle (zero degrees or substantially zero degrees), color flow data, segmentation of the identified vessel adventitia.

In some embodiments, redundant data sets with the transducer in the same physical position are compared to identify regions within the vessel lumen where there is speckle decorrelation. This requires the comparison of two data sets. The decorrelation is used to suppress backscatter from the lumen which improves contrast between the intima and lumen.

Acquisition Angle Optimization

After the data set reduction using the parameters previously discussed, the remaining data which still contain the necessary volume of interest is further reduced prior to calculation of the media-adventitia boundary and intima-lumen boundary by selecting optimal acquisition angles so the entire vessel perimeter may be assessed. It is assumed that the stored ultrasound data interrogated the volume of interest at multiple vector angles for each transducer position.

The arterial wall under ultrasound insonification tends to behave more like a specular reflector rather than an omnidirectional backscatter. This is due to the general make-up of the arterial wall which consists of the adventitia, media and intima. This reflective behavior of arteries such as the carotid makes it difficult to obtain optimal ultrasound images for the entire artery circumference without slightly tipping or tilting the transducer. Use of multiple acquisition angles for a given transducer position circumvents this behavior to obtain maximum contrast between the lumen and entire vessel circumference as well as reduce speckle noise (see, e.g.; A. Lorenz, L. Weng, and H. Ermert, "A Gaussian model approach for the prediction of speckle reduction with spatial and frequency compounding," in 1996 IEEE Ultrasonics Symposium. Proceedings, 1996, vol. 2, pp. 1097-1101; and S. K. Jespersen, J. E. Wilhjelm, and H. Sillesen, "Multiangle compound imaging.," Ultrason. Imaging, vol. 20, pp. 81-102, 1998, the entireties of which are hereby incorporated by reference herein and made part of the present disclosure).

Figure 7:
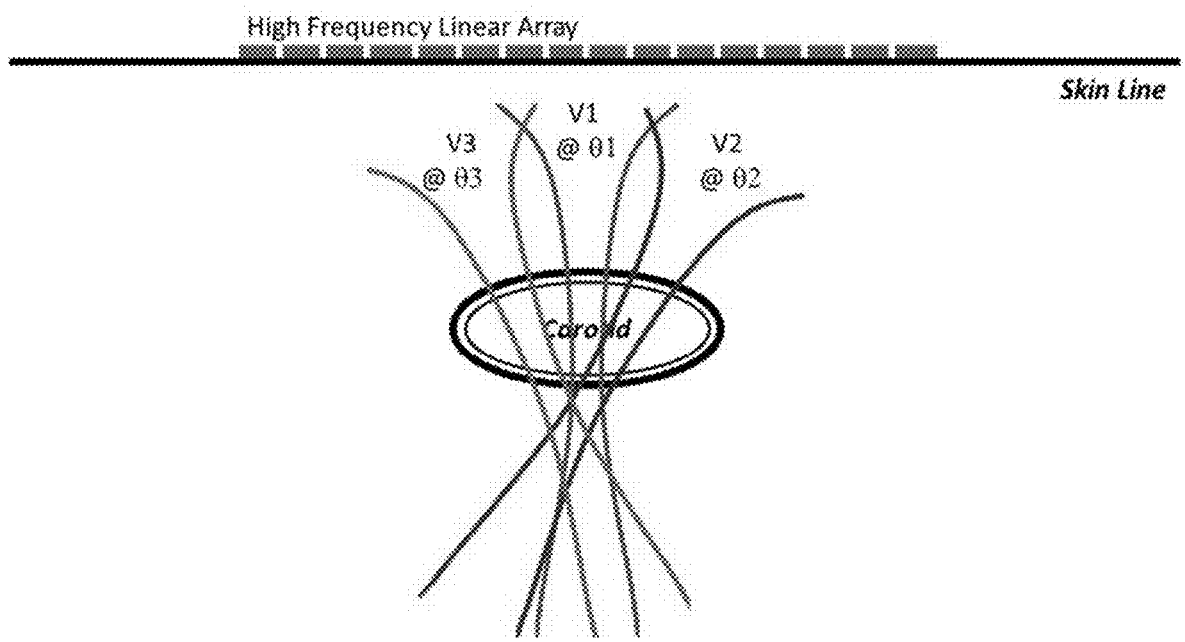
FIG. 7 illustrates how multiple views of the same vessel of interest (VOI) are obtained by steering the ultrasound beam at different angles for a given transducer position.

Multiple views of the same vessel of interest (VOI) are obtained by steering the ultrasound beam at different angles (FIG. 7) for a given transducer position. Although this method has been primarily used to reduce speckle artifacts; it also enhances the arterial wall when applying processing steps which emphasize the artery wall and lumen and deemphasizes the other speckle. FIG. 7 shows the primary premise of steering the ultrasound vector. In some embodiments, the artery of interest is insonified by three different angles, $\theta_1$, $\theta_2$, and $\theta_3$. The three different angles permit the combining of three different data sets of the artery of interest to reduce speckle and improve the calculation of the media-adventitia and intima-media boundaries.

The data from the multiple acquisition angles may be combined immediately prior to the boundary calculation. In some embodiments, the disclosed apparatus creates an average of the three data sets by either adding the final of each image together or averaging the preprocessed data together with each image weighted based on the angle to the carotid wall and lumen to enhance the contrast. In some embodiments, the apparatus creates a final data set based on maximum values of the data sets at multiple angles. In some embodiments, the apparatus generates a final data set based on minimum values of the data sets at multiple values. In some cases, the apparatus creates the data set which is based on the average, maximum, or minimum values of the three images and the angle made to the artery wall. In some embodiments, the ultrasound apparatus processor compares the ultrasound data set contrast of the wall and lumen to determine the angles used in the final representation and analysis.

In another embodiment, the boundaries for each identified acquisition angle are first determined and then later combined to determine the boundaries around the entire vessel throughout the entire volume.

FIG. 7. Insonification of the VOI (carotid) with many different acquisition angles $$I_{total}(x,z)=1/N\Sigma_{i=1}^{N}I(x,z,\theta_i) \quad (1a) <average>$$

$$I_{total}(x,z)=\Sigma_{i=1}^{N}\max(I(x,z,\theta_i)) \quad (1b) <maximum\ intensity>$$

$$I_{total}(x,z)=\Sigma_{i=1}^{N}\min(I(x,z,\theta_i)) \quad (1c) <minimum\ intensity>$$

$$I_{total}(x,z)=\Sigma_{i=1}^{N}w(x,z,\theta_i)*I(x,z,\theta_i) \quad (1d) <weighted\ average>$$

Equations 1a through 1d show some of the basic calculations for creating the final ultrasound data set. 'x' and 'z' are the spatial locations in the ultrasound data, $\theta_i$ are the steering angles used to acquire the image, 'i' is the angle index and 'w' is the weight assigned to the specific image data which may be a function of spatial location. Typically, a steered angle which is more orthogonal to the arterial wall will have a greater weight because there is a greater chance of obtaining a strong echo.

Figure 8A:
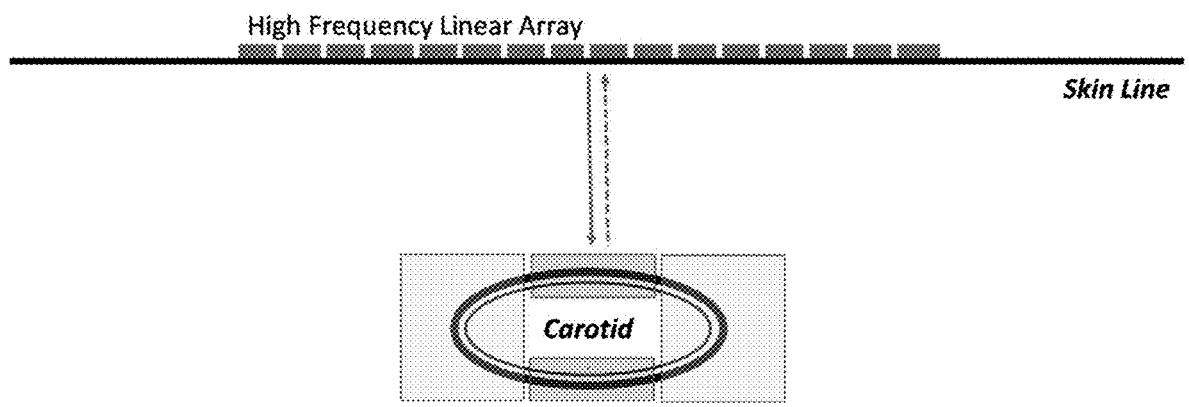
FIGS. 8a-c show how imaging the carotid at different angles improves the overall visibility.
Figure 8B:
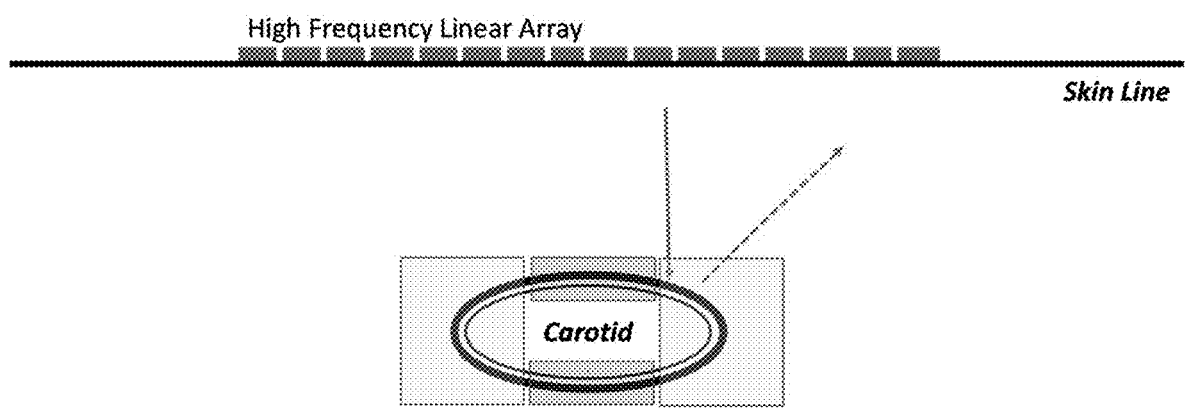
Figure 8C:
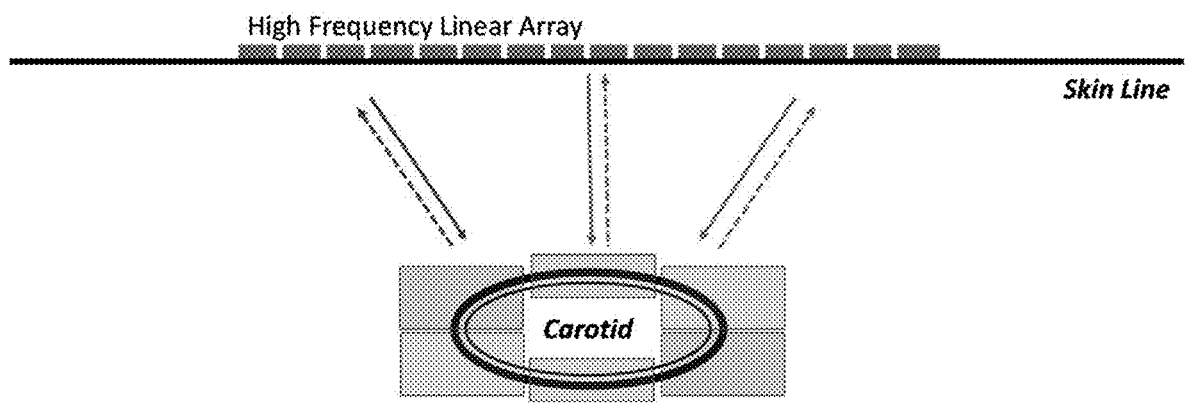

Although the following description focuses on the carotid, it is important to note that these same techniques apply to other vessels such as the femoral artery. FIGS. 8a through c show how imaging the carotid at different angles improves the overall visibility. If just the original angle were used, then it is highly possible that only part of the carotid would be visualized and the boundary around the entire vessel perimeter would be difficult to determine.

Methods to Determine Acquisition Angle

There are multiple methods to determine the ideal acquisition angle for the vessel through adaptive methods. These methods include:
1. Vessel wall slope extrapolation;
2. Color flow perimeter fitting and segmentation;
3. Adventitia segmentation; and
4. Virtual apertures.

Each of these methods is described in detail below.

Methods to Determine Acquisition Angle: Vessel Wall Slope Extrapolation

Although FIGS. 7 and 8 show the advantages of ultrasound data sets at multiple angles to better visualize a specular reflector like an arterial wall, there are also some disadvantages. One of the disadvantages is the reduction in frame rate which causes an increase in acquisition time and total data acquired. The frame rate reduction is simply proportional to the inverse of the number of steering angles required. Methods to reduce the number of steering angles required minimizes this effect. Application of RF techniques is another option that circumvents the frame rate reduction at the cost of possible reduced signal-to-noise ratio (SNR) and the requirement of more offline computational capabilities. The combination of both adaptive imaging and RF techniques may also achieve these goals.

Since the ultrasound data was previously recorded, the acquisition angles have already been prescribed. Vessel wall slope extrapolation determines the optimal interrogation angle for each transducer position and determines the vessel perimeter where the acquisition angle is valid.

Figure 9:
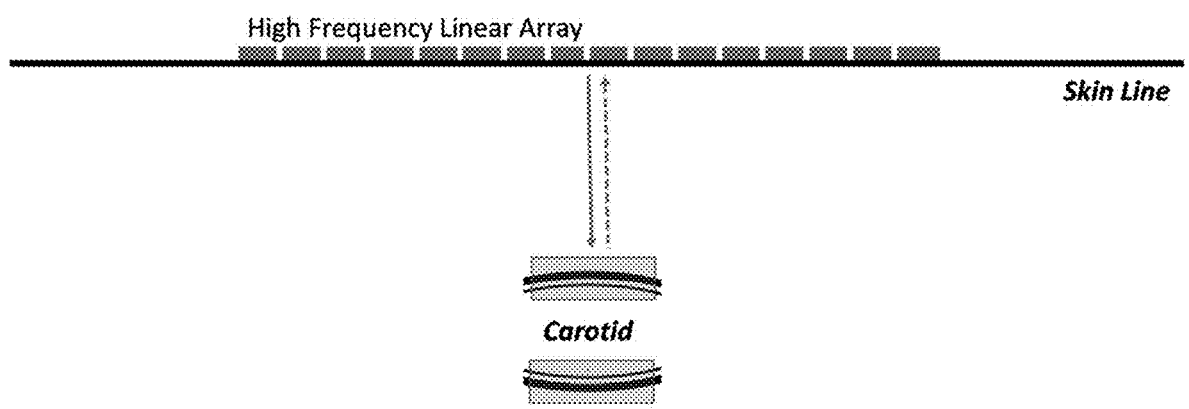
FIG. 9 shows the carotid again and how the typical ultrasound beam that is normal to the high frequency linear array is typically unable to detect the sides of the carotid. However, this initial image allows the apparatus to possibly infer the ideal steering angle to visualize the sides of the carotid rather than utilizing multiple angles that may be redundant or possibly not necessary.

FIG. 9 shows the carotid again and how the typical ultrasound beam 802 along a first angle that is normal to the high frequency linear array is typically unable to detect the sides of the carotid. However, this initial image allows the disclosed apparatus to possibly infer the ideal steering angle to visualize the sides of the carotid rather than utilizing multiple angles that may be redundant or possibly not necessary.

FIG. 8a) The carotid insonified by one imaging angle 802. The carotid wall in the first region 810 is easily viewed. b) As the carotid turns downward, the specular behavior of the reflection prevents the imaging apparatus from showing clear visibility in second (e.g., lateral) regions 804 wherein the imaging angle is not normal to the wall of the carotid c) If multiple visualization angles (e.g., the first angle 802, a second angle 820, and a third angle 830) are used, then carotid perimeter is visualized with optimal brightness and contrast to the lumen. For example, the second angle 820 can be used to visualize portions 840 of the regions 804 and the third angle 830 can be used to visualize portions 850 of regions 804.

Figure 10:
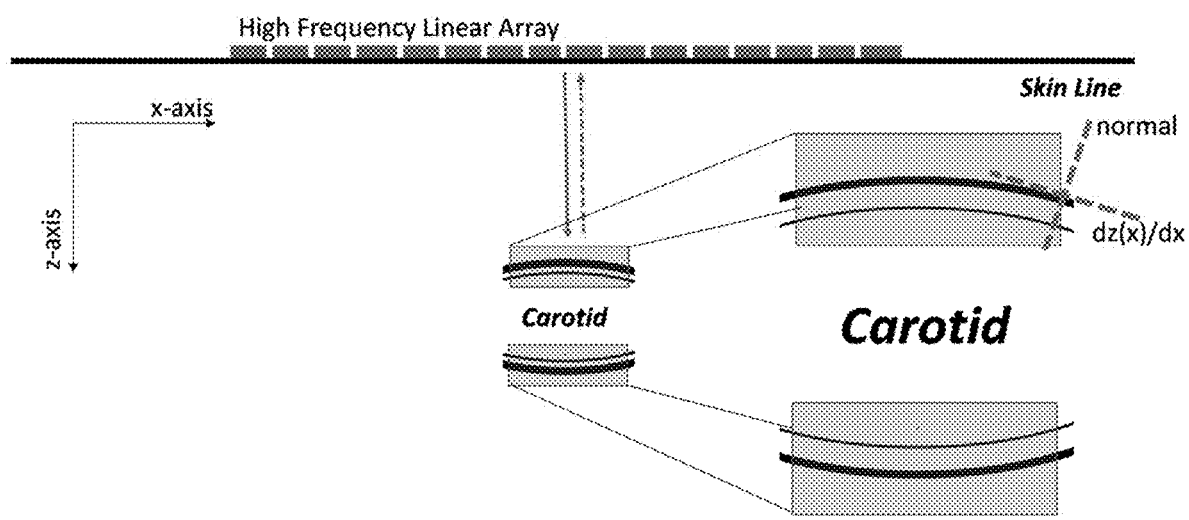
FIG. 10 illustrates how, in some embodiments, the ideal acquisition angle is estimated by calculating the slope of the carotid wall near the edges.

In some embodiments, the ideal acquisition angle is estimated by calculating the slope of the carotid wall near the edges as shown in FIG. 10. For example, suppose the slope is calculated in the ultrasound data at a point $(x_s,z_s)$ where the slope is:

$$\text{slope} = \frac{dz(x)}{dx} \quad (2)$$

which assumes that the wall curvature is partially identified. In this case, the angle, which is normal to the slope of the carotid on the edges is described as:

$$\text{slope}_n = \frac{-1}{\frac{dz(x)}{dx}} \quad (3)$$

Figure 11:
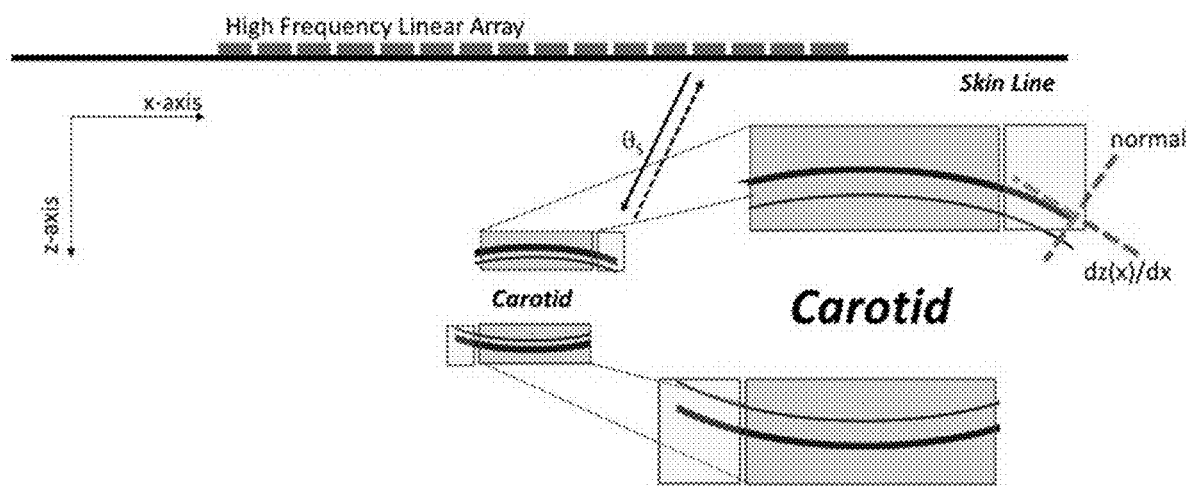
FIG. 11 illustrates how, after the new data are selected using the appropriate steered angle, the slope at the new edge is again estimated to determine the next steering angle.

The normal to the slope ($\text{slope}_n$) is expressed as a fraction A over B and therefore the steered angle is:

$$\theta_s = \tan^{-1}\left(\frac{A}{B}\right) + \frac{\pi}{2} \quad (4)$$

where the $\pi/2$ is equivalent to 90 degrees to put the angle the frame of transducer. After the new data are selected using the appropriate steered angle, the slope at the new edge is again estimated to determine the next steering angle (FIG. 11). The number of available discrete steering angles may be determined a priori based on transducer performance. Echo data obtained with a new steering angle would be selected if there is sufficient change in the slope of the artery wall. Another option is to use echo data obtained with a new steering angle based on the slope change and length of carotid wall detected with the previous steering angle. Either approach is continued until data viewing along the entire carotid has been completed.

Again, it is important to note that the adaptive acquisition angle may be accomplished during the data acquisition phase. If applied during the acquisition, then the data stored is reduced since data with poor steering angles are not saved. If applied during the analysis phase, then a superset of steering angles is analyzed, and the optimal angles are used to assess the boundaries around the artery circumference and the other data is discarded.

Equation 5 is used to determine the weight factor expressed in equation 1d since a transmit and receive angle which is closer to the normal calculated in equation 4 should be weighted more than other images or vectors. For example, in some embodiments, the total weight factor for each spatial location is determined to limit significant brightness and contrast disparities once the ultrasound images are combined. Equation 5 is one example of a weight factor where $\theta_s$ is the angle of the ideal steered ultrasound beam and $\theta_i$ is the actual angle of acquisition. The closer the actual angle of acquisition is to the ideal steered angle, the higher the weight factor. This is only one of many ways to calculate the weight factor.

$$w(\theta_i) = \cos(\theta_S - \theta_i) \tag{5}$$

Figure 12:
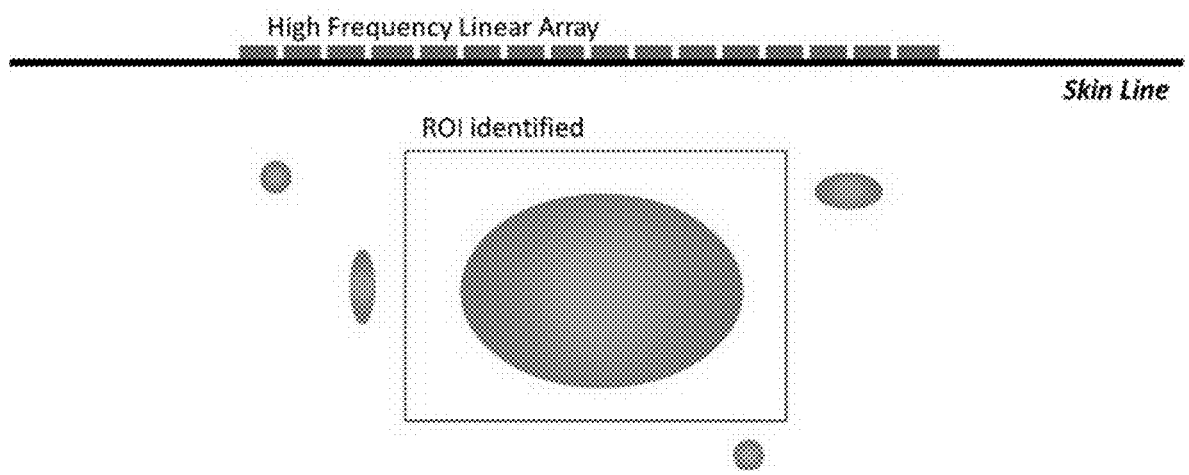
FIG. 12 illustrates flow detected using power Doppler.
Figure 13:
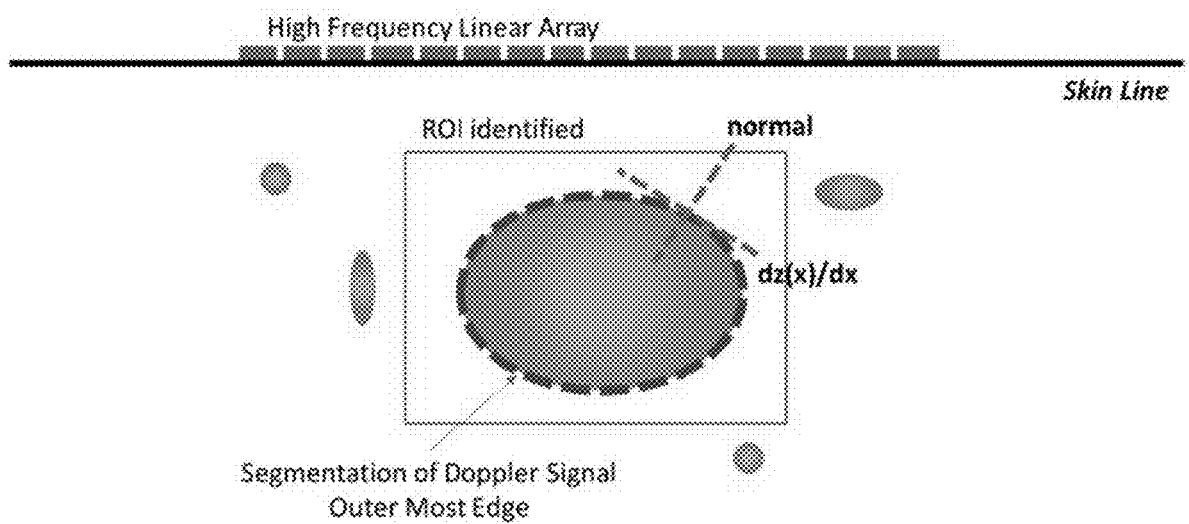
FIG. 13 illustrates how segmentation has occurred and the estimates of the normal around the carotid have been computed to determine ideal steering angles.

Methods to Determine Acquisition Angle: Color Flow Perimeter Fitting and Segmentation Another method to determine the necessary angles rather than using the iterative approach just mentioned, is the application of color flow, power Doppler or speckle statistics. In some embodiments, described herein, visual differentiators other than color can be used to convey desired features. For example, grayscale, hatching, and/or other differentiators may be used. The advantage of using flow measurements rather than conventional B-mode is the entire outline of the carotid may be determined. This permits immediate segmentation of the outermost edge of the flow pattern for calculation of optimal acquisition steering angle. FIG. 12 shows flow detected using power Doppler. The size of the flow region identifies the carotid. In FIG. 13, segmentation has occurred and the estimates of the normal around the carotid have been computed to determine ideal steering angles.

Figure 14A:
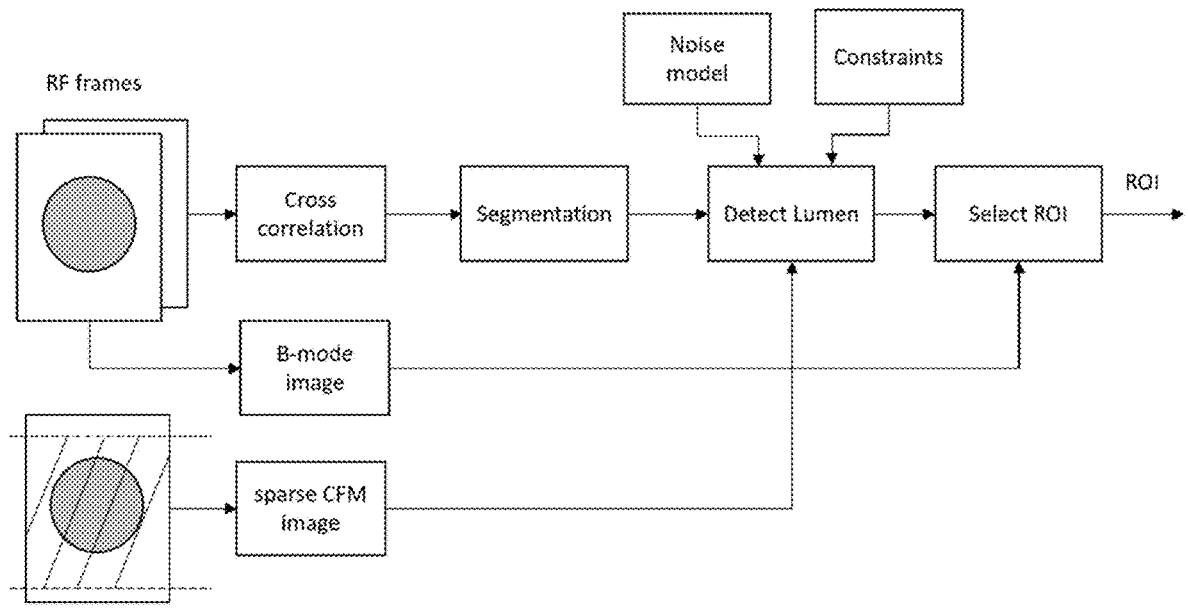
FIGS. 14a-c illustrate methods of automatically detecting a region of interest (ROI) (e.g., a volume of interest (VOI)).

FIG. 14a shows another method 1400 for lumen identification and segmentation of the lumen. In this approach for every acquisition data set. 3 data sets are acquired—2 B-mode sets 1402, and 1 color flow map (CFM) set 1404, where the CFM is sparse. A sparse CFM frame 1404 contains 24 to 32 lines spanning a lateral image of about 3 cm, Each CFM line is acquired with 8 to 16 shots.

A processor produces a map of the normalized cross-correlation 1406 of the RF data from the B-mode images 1402. The map is then segmented 1408 by thresholding and contiguous regions with low values of the cross correlation are labeled. The lumen of the carotid artery is identified (e.g., detected) by combining the segmented regions with low cross correlation and the sparse CFM image. A candidate for a lumen in the echo data is a contiguous region with low cross correlation intersected by a CFM line that has estimated valid flow within the region. The selection is further regularized by using a noise model to reject regions with low SNR and physiological constraints to reject regions whose shape, size and position do not match the physiological constraints.

Figure 14B:
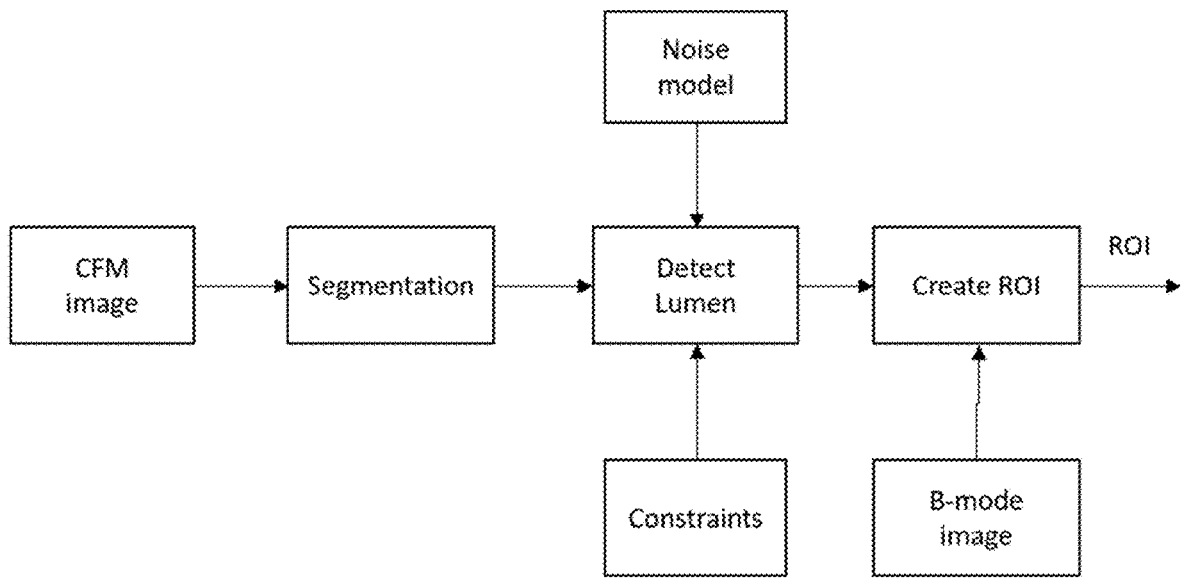
Figure 14C:
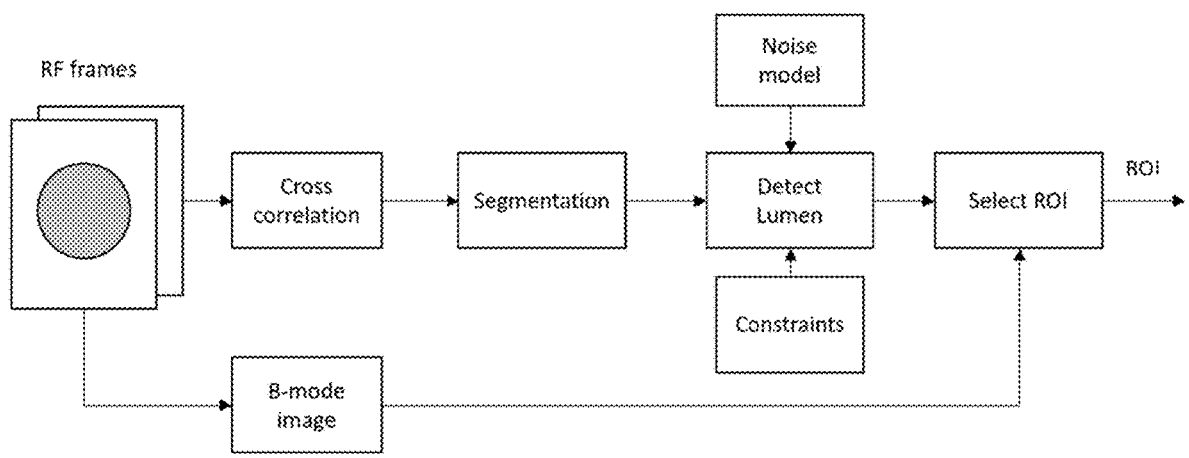

FIG. 14. a) Automatic VOI (e.g., ROI) detection 1400 using normalized correlation of B-mode RF data and sparse CFM image b) Automatic VOI detection 1420 using CFM and B-mode images c) Automatic VOI detection 1460 using correlation of RF frames and B-mode data The previous methods describe using power Doppler or a combinational approach (B-mode RF and sparse CFM methods) to identify the vessel-of-interest. Other methods are also applicable such as combining duplex data sets (e.g. B-mode and CFM) or correlation of only the RF data (FIGS. 14b and 14c). In both cases, two or more data sets are required to identify the vessel of interest. In the first case, the data sets are a B-mode and CFM respectively with the transducer held in one spatial position. Similarly; in the second case, at least two RF data sets are used to identify the lumen based on the amount of decorrelation with the transducer held in one spatial position.

Methods to Determine Acquisition Angle: Adventitia Segmentation

The previous adaptive ultrasound angle method utilized the identified edges of the carotid wall to recommend the other acquisition angles to optimize the contrast between the lumen and wall thus yielding ideal IMT measurements on each slice. This is performed along each slice to yield an IMV measurement for the longitudinal axis of the carotid.

Figure 15:
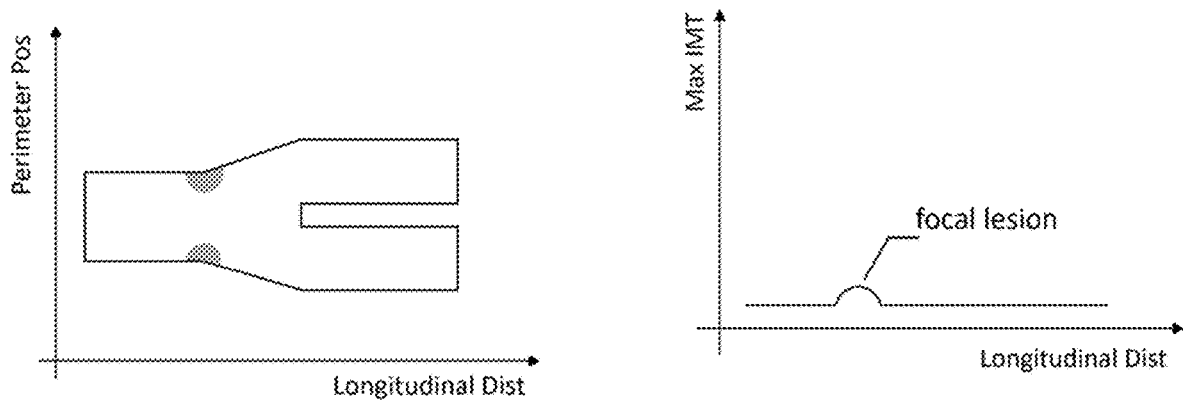
FIG. 15 shows two ways of graphing the data from adaptive angle methods type (note: data has not been included). The first graph displays the intimal-media thickness (IMT) as a function of longitudinal position and perimeter position around the vessel. The second graph just displays the maximum IMT as a function of longitudinal position in the vessel.

Another adaptive angle technique immediately segments the carotid based on the adventitia. The adventitia of the artery is usually visualized without steering the beam. This implies that the adventitia may be segmented and fit with an ellipse. Once the carotid is fit with an ellipse, the optimal steered angles to the wall are determined. If necessary, the added wall-lumen enhancement enables further fine-tuning of the steered angle. The IMT for each steering angle around the carotid perimeter is analyzed and integrated with the other angles. This method continues for each transverse plane along the longitudinal axis to create an IMV map which increases the confidence of whether an atheroma has been located. FIG. 15 shows some creative ways of graphing the data from adaptive angle methods type (note: data has not been included). The first graph displays the IMT 1502 as a function of longitudinal position and perimeter position around the vessel. The second graph just displays the maximum IMT 1504 as a function of longitudinal position in the vessel.

FIG. 15. Possible method of graphing analysis. In the 3D plot, the IMT 1504 determined from each perimeter position comes from different steering angles. The 2D plot takes the maximum IMT 1504 for each longitudinal position.

Methods to Determine Acquisition Angle: Virtual Apertures

Figure 16:
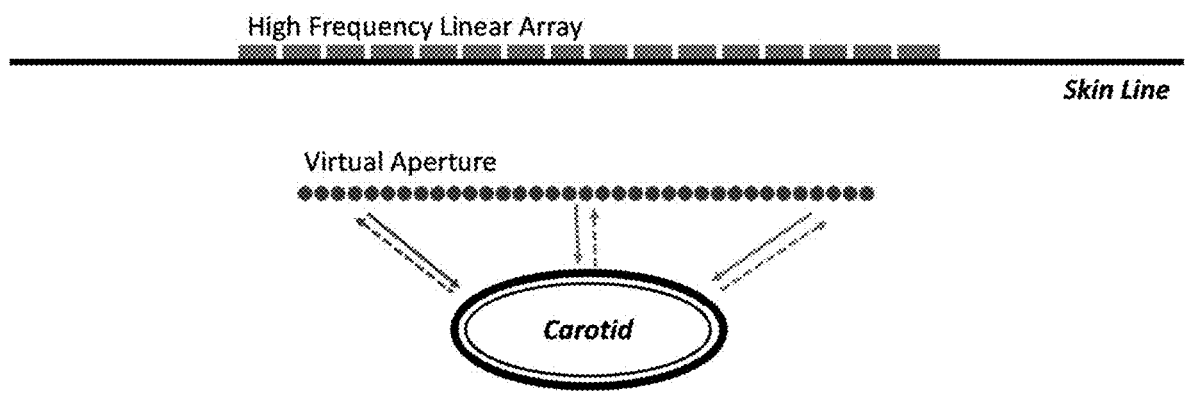
FIG. 16 illustrates a virtual aperture which has been created using a standard high frequency linear array.

A virtual aperture is another method which limits frame rate reduction and post processing steps while enabling multiple angle techniques. FIG. 16 shows a virtual aperture which has been created using a standard high frequency linear array. The circles 1602 (e.g., "dots" or elements) signify a corresponding transmit and receive foci which is considered a separate aperture. The transmit event is identical to the transmit event in a conventional image sequence. However, in this embodiment, the receive focus eliminates dynamic focusing which continuously adjusts the element delays maintaining the receive focus on deeper and deeper targets and just focuses at the same point as the transmit focus. To create the virtual aperture, the receive focus and corresponding delays are maintained on only one position which corresponds to the actual transmit focus throughout the entire acquisition time. In some embodiments, the disclosed apparatus has stored the fixed transmit and receive foci data which defines the virtual aperture. Essentially, these individual foci equate to the individual elements in the transducer. The signal at each virtual element is expressed as:

$$S_{x_n, y_n}(t) \tag{6}$$

Since the physical position is known as well as each time vector, it is possible to place appropriate transmit and receive delays on the signal at this element location to equate to an actual aperture.

$$S_{x_n, y_n}(t + \delta_{tx, x_n, y_n}(x,z) + \delta_{rx, x_n, y_n}(x,z)) \tag{7}$$

Furthermore, since the aperture is virtual and each transmit and receive vector is calculated after listening to the signal at one physical point, then the vectors may be steered and focused to multiple locations both in front of and behind the virtual aperture. This allows for multiple transmit and receive angles to be used when imaging the VOI albeit post acquisition, which permits optimal detection of the carotid artery wall.

FIG. 16. Creation of a virtual aperture in order to obtain multiple acquisition angles of the carotid FIG. 17. Each 'dot' is a virtual element in the virtual aperture with a signal $S_{x_n,y_n}$ which is a function of time The signals from the virtual elements with the appropriate delays are used to create multiple image vectors through a summation process.

$$V_m(x,z)=\Sigma_{n=1}^N S_{x_n,y_n}(t+\delta_{tx,x_n,y_n}(x,z)+\delta_{rx,x_n,y_n}(x,z)) \qquad (8)$$

where $V_m$ is the vector for the image.

Figure 17:
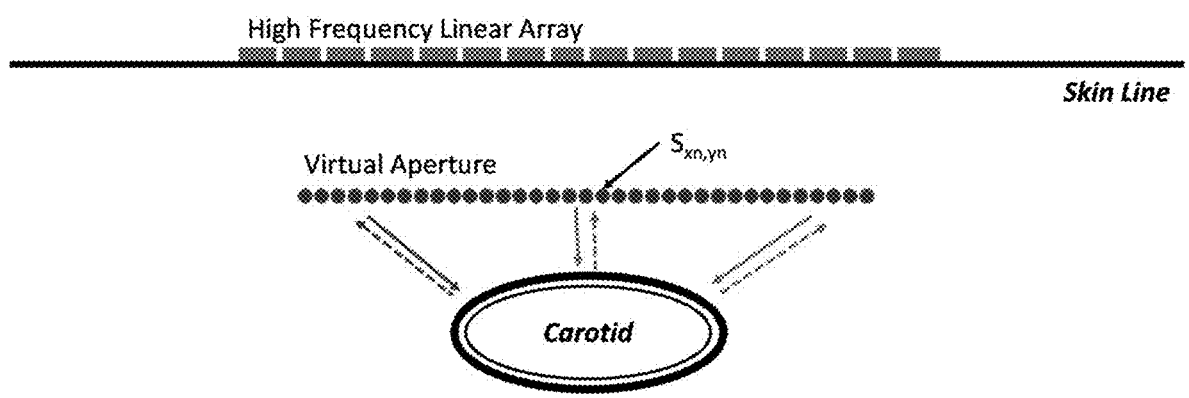
FIG. 17 illustrates a virtual aperture wherein each 'dot' is a virtual element in the virtual aperture with a signal $S_{xn,yn}$ which is a function of time.
Figure 18:
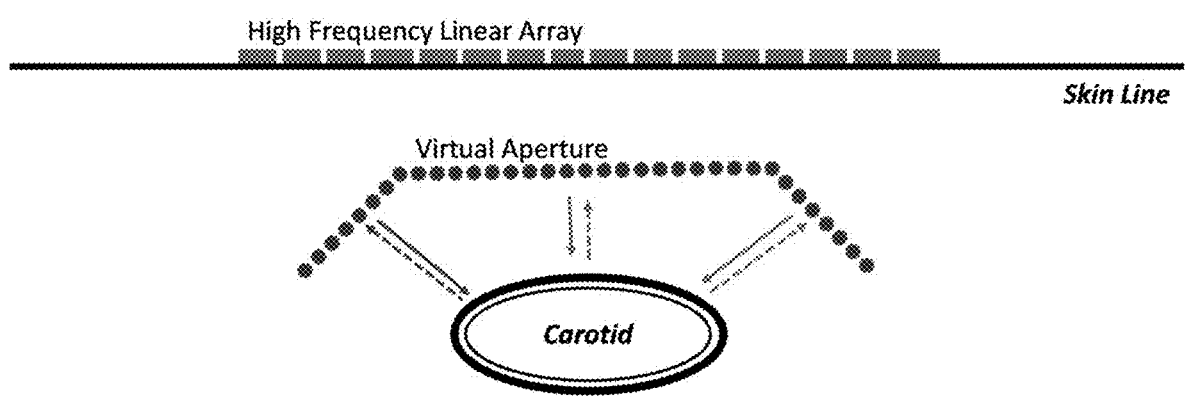
FIG. 18 illustrates a virtual aperture that has different depth locations for the elements, which based on the location of arterial walls, may be superior to using just one depth.

FIGS. 17 and 18 show the elements 1602 of the virtual aperture are located parallel to the real elements of the high frequency linear array. Although this aligns with conventional ultrasound systems that typically fix the transmit focus at one specific depth, this may not be ideal when applied to optimizing the carotid image. FIG. 18 shows a virtual aperture that has different depth locations for the elements 1602, which based on the location of carotid walls, may be superior to using just one depth.

In some embodiments, the disclosed apparatus creates virtual apertures with 3D data to also obtain optimal insonification angles to the carotid. The virtual aperture technique also shows the importance of keeping the carotid in the middle (or nearly the middle, e.g., +/−0-20% from a center point) of the linear array span.

Additional Methods to Improve Vessel Boundary Detection
Dynamic Range Compression After the optimized data are determined for the volume of interest, the remaining ultrasound data are further processed to identify the vessel. One method is the use of dynamic range compression, which is a uniquely designed amplitude filter that is also spatially sensitive and keeps backscatter from the lumen or the vessel wall while other data are removed. This process enables improved identification of vessel regions. Dynamic range compression is used prior to identification and segmentation of the media-adventitia or lumen-intima boundaries.

Speckle Reduction Filtering

Another method to enhance the visibility of the vessel is with a speckle reduction filter (see, e.g., A. Lorenz, L. Weng, and H. Ermert, "A Gaussian model approach for the prediction of speckle reduction with spatial and frequency compounding," in 1996 IEEE Ultrasonics Symposium. Proceedings, 1996, vol. 2, pp. 1097-1101). As previously mentioned, the vessel lumen contains low amplitude backscatter, which decorrelates temporally since it contains the blood flow. The vessel wall is a specular reflector and visibility is highly dependent on the ultrasound acquisition angle that is optimized through multiple methods. The other regions of the acquisition usually contain speckle which follows specific statistics that are related to the transducer characteristics. When the transducer is in a fixed position acquiring multiple data sets, the speckle backscatter outside of the vessel is stationary and will not have the same mean amplitude as inside the lumen. This allows automatic suppression of the speckle backscatter which enables extraction of the vessel of interest with a higher level of confidence.

Signal Coherence on Each Transducer Element

If the ultrasound data contains RF data from each transducer element, then coherence methods are used for each acquisition to separate tissue echoes (e.g., return echoes) from spurious noise. There are several methods that calculate the coherence between elements to improve signal-to-noise ratio and contrast (see, e.g., Li, Pai-Chi and Li, Meng-Lin, "Adaptive Imaging Using the Generalized Coherence Factor", IEEE Transactions on Ultrasonics, Ferroelectrics and Frequency Control, vol. 50, no. 2, pp. 128-141; and Camacho, Jorge, Parilla, Montserrat, and Fritsch, Carlos, "Phase Coherence Imaging", IEEE Transactions on Ultrasonics, Ferroelectrics, and Frequency Control, vol. 56, no. 5, pp. 958-974, the entireties of which are hereby incorporated by reference and made part of the present disclosure). In some embodiments, the disclosed apparatus applies the generalized coherence factor or a phase coherence factor and sign coherence factor to RF data after the optimized ultrasound data are identified.

Matched Vessel Filter

The temporally and spatially registered volume of interest allows an identified lumen or vessel wall for one transducer position to be applied spatially adjacent transducer positions. In some embodiments, the previous ultrasound data set and identified vessel of interest for one transducer position is applied to the adjacent data set for fast and effective localization of the vessel wall or lumen. This process of using the adjacent data set as the filter for adjacent ultrasound data is used for the entire volume of interest. This matched filter approach has a high likelihood of optimizing the signal-to-noise ratio around the vessel prior to determine of the boundaries.

Figure 19:
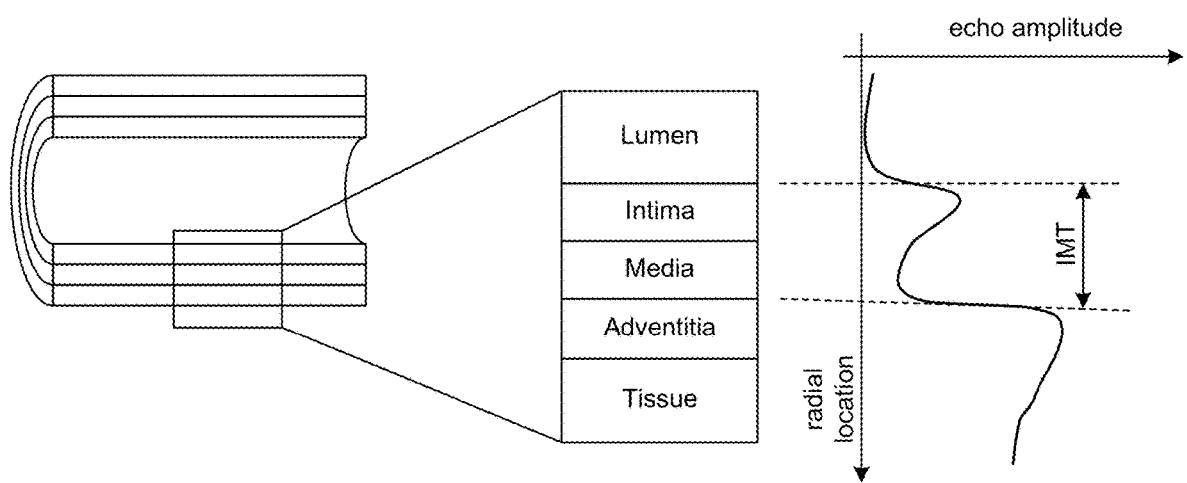
FIG. 19 illustrates a cross-sectional sketch of the vessel which consists of multiple layers. These layers consist of the adventitia, media, and intima. The lumen is the center of the vessel where the blood flows. The entire vessel is surrounded by tissue.

Boundary Calculation: MAB and LIB
Media-Adventitia Boundary (MAB) Contour Determination FIG. 19 shows a cross-sectional sketch of the vessel which consists of multiple layers. These layers consist of the adventitia, media, and intima. The lumen is the center of the vessel where the blood flows. The entire vessel is surrounded by tissue. FIG. 19 also includes a plot of echo amplitude between the multiple layers, lumen and tissue with the origin at the lumen center. The adventitia typically has the strongest echo, which is highly sensitive to the incident angle of the ultrasound. The echo amplitude decreases in the media and then slightly increases again in the intima. The intima-media thickness (IMT) is determined by distance between the media-adventitia boundary (MAB) and the lumen-intima boundary (LIB). In some embodiments, the MAB is determined by analyzing the brightness of the ultrasound echoes (e.g., return echoes). In another embodiment, the adventitia is identified through the intensity of the echoes and specular behavior of the echo. The tissue is identified through the speckle statistics and the lumen is identified by the intensity of the echoes and speckle decorrelation when the transducer is stationary. The ability to accurately and precisely identify the boundaries as diagramed in FIG. 19 is dependent on the transducer design. For example, if the transducer is designed to operate at a high frequency that improves axial resolution and minimizes the possibility of off axis scatterer interference, then the delineation between the lumen-intima and media-adventitia boundaries may be vastly improved. Ideally, the axial and lateral resolution of the transducer is less than 100 microns. In the case of the extracranial carotid, acquisition includes the carotid volume from the clavicular notch to slightly beyond the bifurcation. It is possible to automatically determine the IMT at each location along this vessel length by automatically calculating the IMT as the distance between the edges of the two peaks in the echoes shown in FIG. 19 (see, e.g., F. Molinari, G. Zeng, and J. S. Suri, "A state of the art review on intima-media thickness (IMT) measurement and wall segmentation techniques for carotid ultrasound,"

Comput. Methods Programs Biomed., vol. 100, no. 3, pp. 201-221, 2010; A. C. Rossi, P. J. Brands, and A. P. G. Hoeks, "Automatic localization of intimal and adventitial carotid artery layers with noninvasive ultrasound: a novel algorithm providing scan quality control.," Ultrasound Med. Biol., vol. 36, no. 3, pp. 467-79, March 2010; J. Canny, "A Computational Approach to Edge Detection," IEEE Trans, Pattern Anal. Mach. Intell., vol. PAMI-8, no. 6, pp. 679-698, 1986; D. E. Ilea, C. Duffy, L. Kavanagh, A. Stanton, and P. F. Whelan, "Fully automated segmentation and tracking of the intima media thickness in ultrasound video sequences of the common carotid artery," IEEE Trans. Ultrason. Ferroelectr. Freq. Control, vol. 60, no. 1, pp. 158-177, January 2013; and M. Demi and M. Paterni, "The first order absolute moment in low-level image processing," in Proceedings of 13th International Conference on Digital Signal Processing, vol. 2, no. 1, pp. 511-514, the entireties of which are hereby incorporated by reference herein and made part of the present disclosure). The integration of the IMT along this vessel length provides more accurate calculation of the intima-media volume (IMV) as well as an increased confidence on the identification of possible atheromas when compared to conventional methods.

Following the definition of IMT from FIG. 19, the goal of the Media/Adventitia Contour Block (FIG. 20) defining steps performed by a processor is to find the location of the rising edge of the echo in radial direction, from lumen center outwards. Edges are detected using an edge detection algorithm such as Canny edge detector. The application of such an edge detector on ultrasound data results in many contours, and this block performs two main tasks (a) minimize the number of edges via image smoothing; (b) narrow the search region for the edge using a priori knowledge about the nature of the echoes.

In some embodiments, the estimation 2000 of the contour of the media/adventitia boundary consists of the following steps (see FIG. 20): preprocessing 2002; remapping of data from Cartesian to polar coordinates 2004; image enhancement 2006; peak detection 2008; media/adventitia VOI selection 2010; edge detection 2012; and edge smoothing 2014.

Step 1, Preprocess 2002. First, the data are conditioned using preprocessing methods which consists of (a) envelope detection; (b) dynamic range compression; (c) adaptive spatial compounding; (d) application of a speckle reduction filter (see, e.g., A. Lorenz, L. Weng, and H. Ermert, "A Gaussian model approach for the prediction of speckle reduction with spatial and frequency compounding," in 1996 IEEE Ultrasonics Symposium. Proceedings, 1996, vol. 2, pp. 1097-1101). Many of these steps have already been discussed in the preceding sections.

Figure 20:
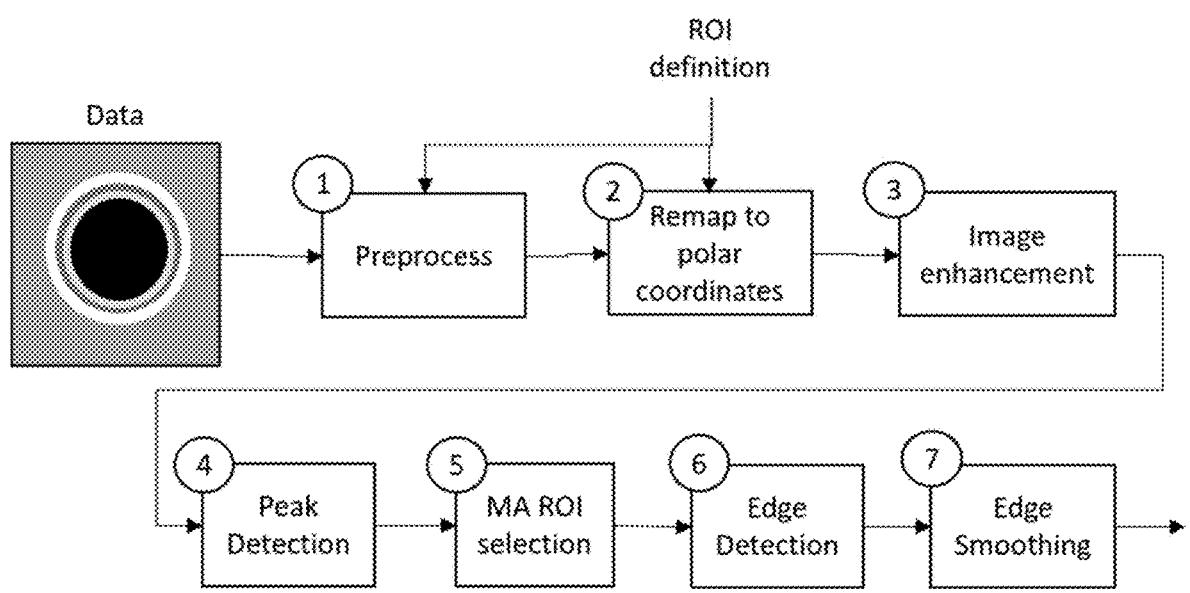
FIG. 20 illustrates a method of estimating the contour of a media/adventitia boundary.
Figure 21:
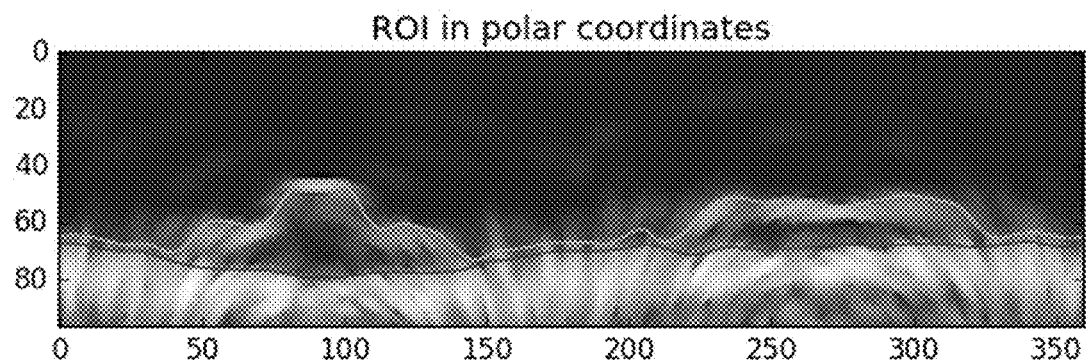
FIG. 21 illustrates an example of re-mapped image data from cartesian to polar coordinates.

Step 2, Remap 2004. The second step as shown in FIG. 20 is to remap the image data from Cartesian to polar coordinates. This remapping enables easier detection of edges along the arterial wall. An example of the resulting image from this operation is shown in FIG. 21. In some embodiments, the center of the polar coordinate system is determined by identifying the lumen through speckle decorrelation and then finding the center of this identified object or lumen. The new coordinate system simplifies the design and application of image enhancement filters. The filters have a large kernel size in lateral dimension (function of angle) and small kernel size in elevation direction (function of radius). This maintains high resolution in the direction orthogonal to the Lumen/Intima and Media/Adventitia boundaries which assists to accurately and precisely detect IMT for one cross-section of the vessel. The remapping makes it also possible to use symmetric boundary conditions in angular direction during the filtration of the image and data regularization. Finally, the remapping simplifies the search for the boundaries and contours, as the search direction now top (center of the vessel) towards the bottom.

Figure 22:
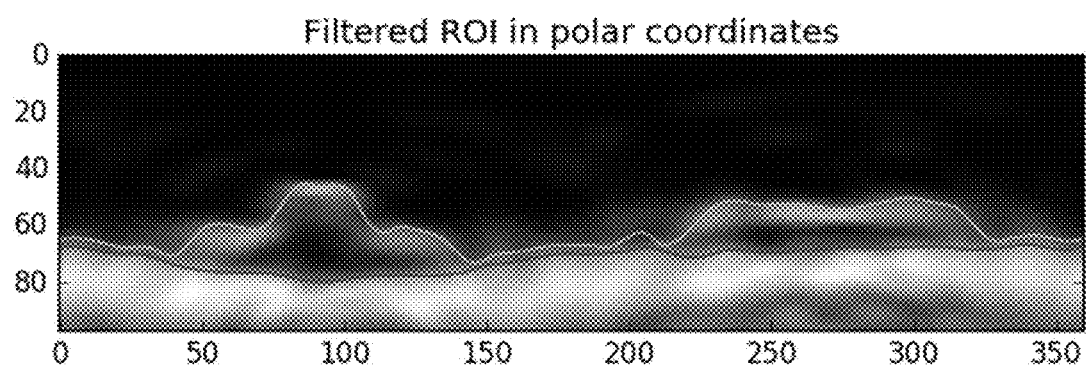
FIG. 22 illustrates an example of an enhanced using an anisotropic smoothing 2D filter.

Step 3, Image Enhancement 2006. Next, the image is enhanced using an anisotropic smoothing 2D filter. It smooths the structures in angular direction while keeping the transitions sharp in radial direction. An example of the result after smoothing is given in FIG. 22. This smoothing operation will reduce the high frequency spatial noise that occurs along wall boundaries.

Step 4, Peak Detection 2008. The next step in the detection of the media/adventitia boundary is to detect the peak echo in radial direction. The peak echo is typically located in the adventitia layer (see, e.g., F. Molinari, G. Zeng, and J. S. Suri, "A state of the art review on intima-media thickness (IMT) measurement and wall segmentation techniques for carotid ultrasound," Comput. Methods Programs Biomed., vol. 100, no. 3, pp. 201-221, 2010 and A. C. Rossi, P. J. Brands, and A. P. G. Hoeks, "Automatic localization of intimal and adventitial carotid artery layers with noninvasive ultrasound: a novel algorithm providing scan quality control.," Ultrasound Med. Biol., vol. 36, no. 3, pp. 467-79, March 2010). The peak detection is done using a simple peak detector.

Step 5, Media-Adventitia (MA) Vessel-of-Interest (VOI) Selection 2010. Selection of narrow region interest around the expected media/adventitia boundary.

Figure 23:
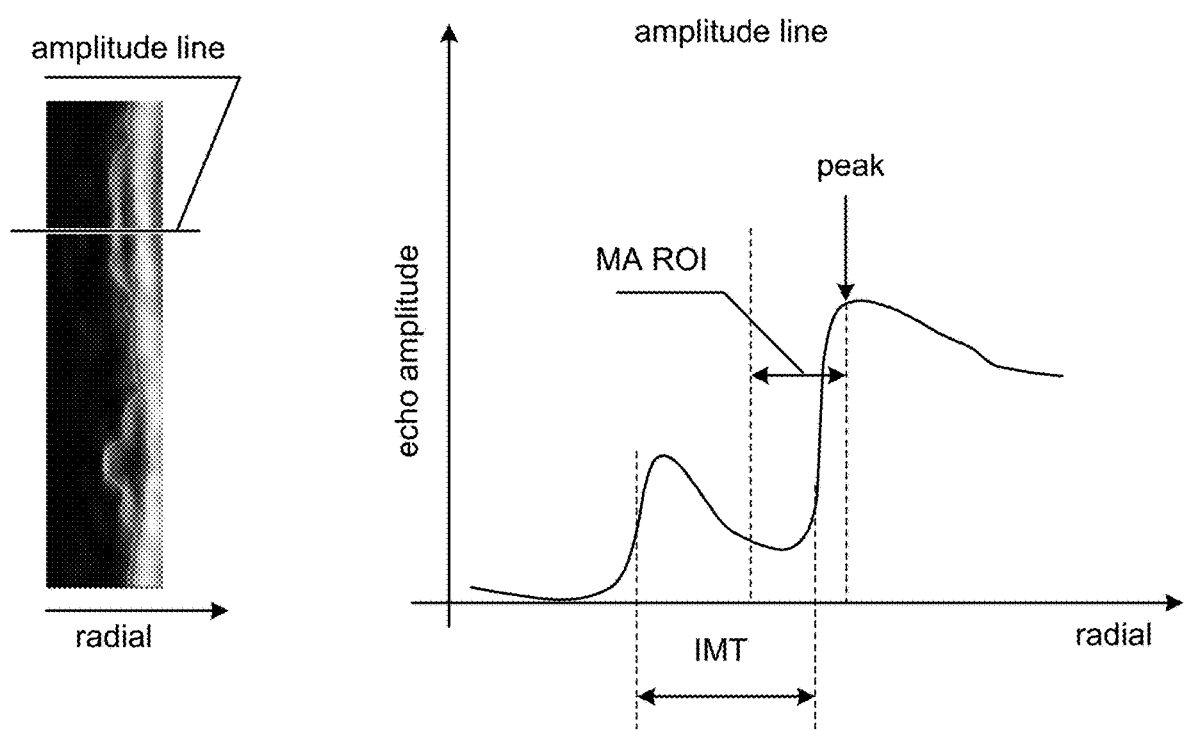
FIG. 23 illustrates the amplitude of a signal in radial direction based on the lumen center used to estimate the intima media thickness. On the left.

FIG. 23 shows the amplitude of the signal in the radial direction based on the lumen center used to estimate the intima media thickness. On the left, FIG. 23 shows the amplitude of the data as a B-mode image. The horizontal axis corresponds to radial direction with the center of the vessel being on the left. The right sub-figure of FIG. 23 shows the amplitude of the signal along a single line. The peak with the highest amplitude belongs to a signal inside the adventitia layer. The MA VOI (e.g., ROI) is selected in the middle between the contour of the lumen (available from the VOI detection) and the position of the peak. In some embodiments, the MA VOI is determined for every single radial direction.

Figure 24:
FIG. 24 illustrates peak echoes (e.g., return echoes) along the radial direction overlaid on top of the B-mode image of the VOI.

FIG. 24. Peak echoes along the radial direction overlaid on top of the B-mode image of the VOI.

Step 6, Edge Detection 2012. The edges are detected using a standard Canny edge detector (see, e.g. J. Canny, "A Computational Approach to Edge Detection," IEEE Trans. Pattern Anal. Mach. Intell., vol. PAMI-8, no. 6, pp. 679-698, 1986). All edges outside of the MA VOI are cleared.

Step 7, Edge (contour) Smoothing (regularization) 2014. The contour of the Media/Adventitia boundary is regularized using a low-pass filter to remove noise from the detection of the position of the edges, and to fill gaps in detected positions.

Lumen-Intima Boundary (LIB) Contour Determination

Figure 25:
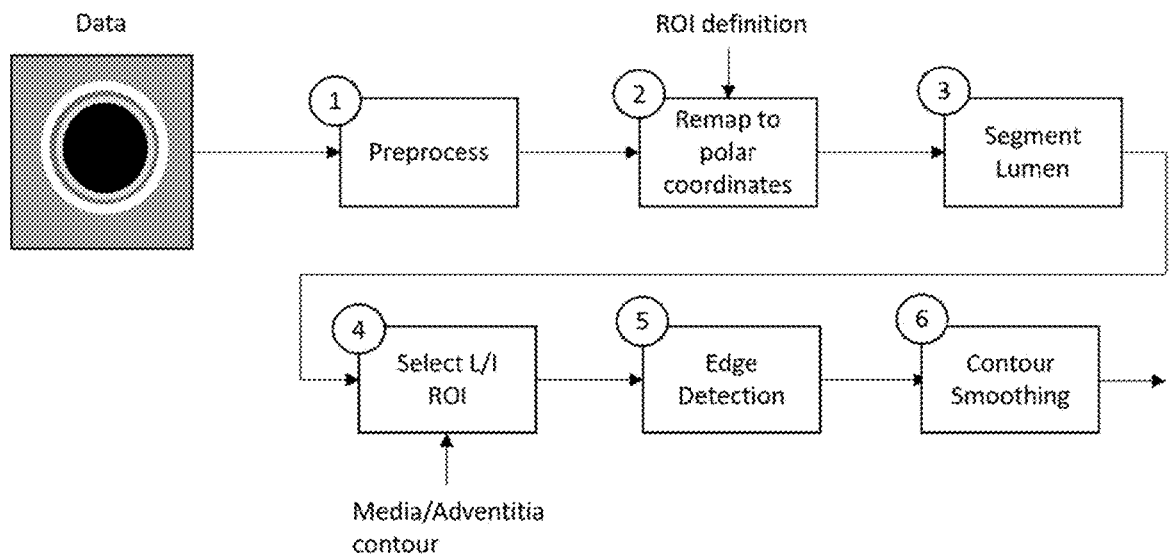
FIG. 25 illustrates an embodiment of a process for detection of the lumen/intima boundary.

The detection 2500 of the lumen/intima boundary is illustrated by the process steps shown in FIG. 25 and is similar to the detection of MAB and consists of preprocessing 2502; remapping of data from Cartesian to polar coordinates 2504; lumen segmentation 2506; VOI selection for contour search 2508; lumen/intima (LI) edge detection 2510; contour smoothing (regularization) 2512.

Step 1, Preprocess 2502. The preprocessing is like the preprocessing for the MAB, where the difference is dynamic range in the dynamic range compression which have already been discussed in the preceding sections. In some embodiments, the dynamic range compression for the LIB is different than the dynamic range compression used for MAB.

Step 2, Remap 2504. Mapping of data from Cartesian to polar coordinates. This step is like the step for the MAB detection where the coordinate system center is determined through lumen identification using speckle decorrelation.

Figure 26:
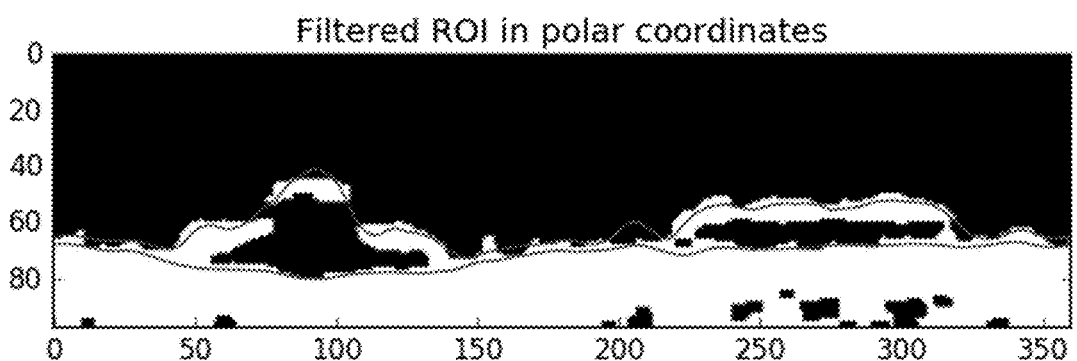
FIG. 26 illustrates a segmented lumen based on the intensity of the data. The threshold for the segmentation is adaptively selected using a gray-level histogram.

Step 3, Lumen Segmentation 2506. The lumen is segmented based on the intensity of the data (FIG. 26). The threshold for the segmentation is adaptively selected using the gray-level histogram (see, e.g., N. Otsu, "A Threshold Selection Method from Gray-Level Histograms," IEEE Trans Sys. Man. Cyber, vol. SMC-9, no. 1, pp. 62-66, 1979, the entirety of which is hereby incorporated by reference herein and made part of the present disclosure.

Step 4, VOI Selection 2508. For every angular position, a start and stop radial distance for a search region for the edge are selected. The search interval is limited between the contour of the segmented lumen and the previously determined contour of the MAB.

Step 5, LI Detection 2510. The edge is detected using a standard edge detection algorithm such as the Canny edge detector. The search is limited only to the boundaries set in (Step 4). The edge closest to the lumen boundary is selected.

Figure 27:
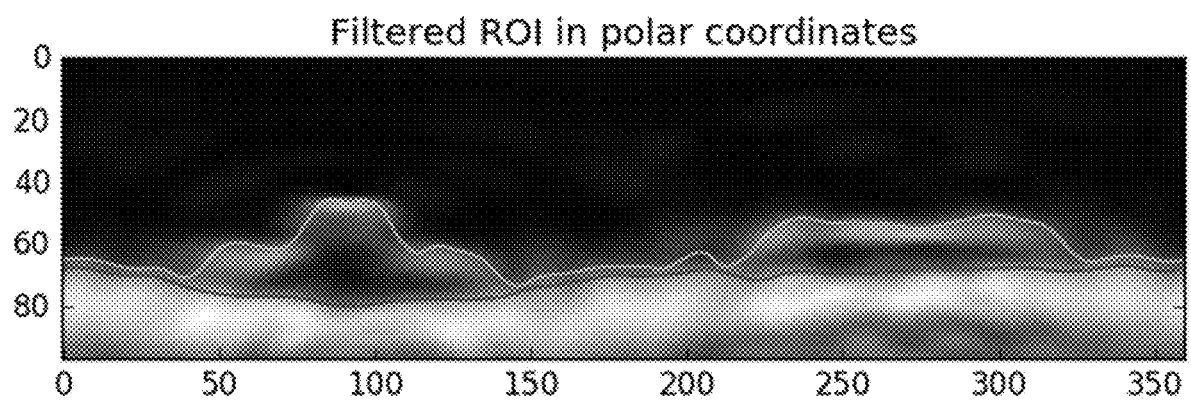
FIG. 27 illustrates data, mapped in polar coordinates with the two contours superimposed.

Step 6; Contour Smoothing 2512. The lumen/intima contour is regularized (e.g.; smoothed) to avoid detection of spurious edges and fill-in missing data points along the contour. FIG. 27 shows the LIB 2702 inside of the MAB 2704, FIG. 27. Data, mapped in polar coordinates with the two contours superimposed.

Quality Assessment of MAB and LIB

Figure 28:
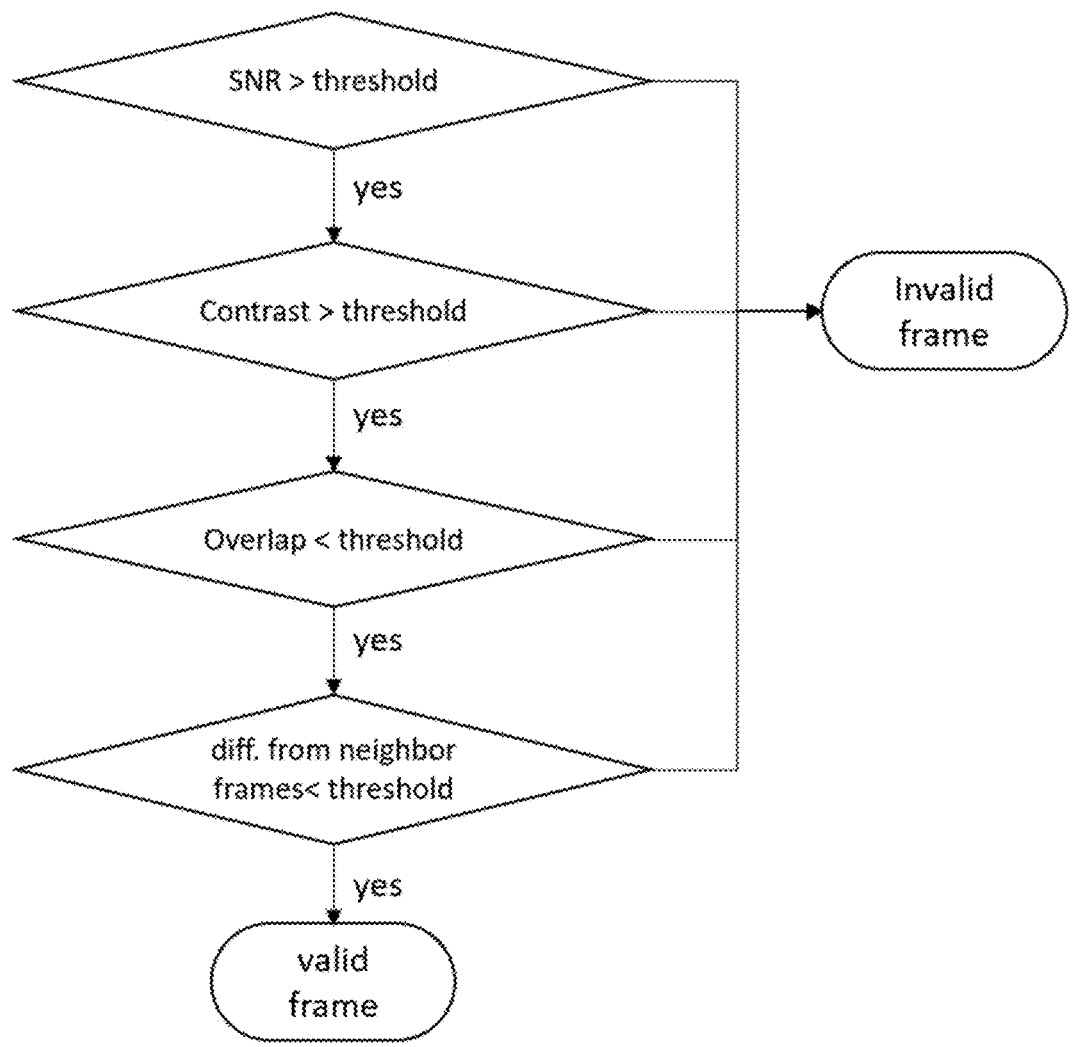
FIG. 28 illustrates a process of classifying the current frame as valid or invalid. The apparatus contains a pre-recorded table with the noise level. The signal level is calculated from the data in the vessel of interest and the signal-to-noise ratio (SNR) is estimated from it. If the SNR is below a pre-set threshold, the acquired ultrasound data plane is invalid.

The quality assessment block is used to reject contours in data acquisition planes where the probability of detecting the LIB and MAB is low. The criteria used for the purpose are: (a) signal to noise ratio of the signal in the VOI; (b) contrast ratio between the echo in the lumen and outside of the lumen; (c) length of the segments where the LIB and MAB contours coincide; (d) the difference of the area surrounded by the LIB and MAB in the current and neighboring data acquisition planes is below a certain threshold. FIG. 28 shows one embodiment of the quality assessment method.

FIG. 28: quality classification of an acquired ultrasound data plane. FIG. 28 illustrates the process of classifying the current frame as valid or invalid. The disclosed apparatus contains a pre-recorded table with the noise level. The signal level is calculated from the data in the vessel of interest and the signal-to-noise ratio (SNR) is estimated from it. If the SNR is below a pre-set threshold, the acquired ultrasound data plane is invalid.

The contrast is calculated as the level of the signal within the lumen (found by the adaptive thresholding) and the signal outside the lumen, but still within the vessel of interest. Low contrast is an indication of the one or more of the following:
1. The receive gain is set too-high for the VOI
2. The scan plane has a high level of clutter
3. The plane that intersects the artery is not the ideal cross-section In any of these cases, the current ultrasound data are invalid.

To successfully estimate the IMT and thus the IMV, there are two distinct echoes from the LI and MA transitions. If the scan plane is oblique to the vessel wall, then at least one of the two specular echoes will be missing. In this case, large portions of the contours will coincide (only one boundary detected). If the total length of these segments exceeds a pre-set threshold, the frame is invalid.

To qualify as an atheroma, the disclosed apparatus looks for the presence of focally elevated IMT found in several contiguous frames, otherwise the detected atheroma maybe an artifact from reverberation. The area surrounded by the LIB and MAB is compared to the areas of the spatially adjacent ultrasound data planes, which are temporally aligned to the cardiac cycle. If the difference in areas is greater than a preselected threshold, then the ultrasound data plane is again invalid.

Data Integration

As was previously discussed, echo data from multiple acquisition angles of the vessel are acquired through the cardiac cycle. This is due to the specular behavior of the vessel wall. In some embodiments, the ultrasound data sets at the optimal acquisition angles are combined prior to determination of the MAB and LIB contours. In another embodiment, the data sets are temporally aligned at the same time in the cardiac cycle, which may be during systole or diastole. The combining of the data sets is done using unprocessed RF data or post-processed echo data. In either case, combination of the data prior to boundary determination necessitates normalization of the data to enable proper identification of either the media-adventitia or intima media boundaries around the entire vessel perimeter. The MAB and LIB detection is determined as previously described.

In another embodiment, the optimal acquisition angles for the entire vessel perimeter with the transducer at the same spatial position are analyzed independently. In this embodiment, the data sets at the different acquisition angles are temporally aligned based on the cardiac cycle. Next, the MAB and LIB of each data set are analyzed. In some embodiments, the center of the polar coordinate system transformation for each data set is based on the average or median of the lumen for all acquisition angles. In another embodiment, the segmentations of each vessel acquisition are combined and then a lumen center is calculated prior to the polar coordinate transformation. This method enables immediate combination of the MAB and LIB contour segments for each acquisition angle. Contour regularization is completed on the combined segments. In another embodiment, the center of the lumen for each acquisition is used prior to boundary detection. Next, the segments of the MAB and LIB for each acquisition angle are combined by determining the spatial transformation between the two polar coordinate systems. Again, regularization is done on the combined MAB and LIB segments independently.

IMV Calculation

The IMV calculation is the integration of the IMT along the entire length of the detected artery of interest, which in one embodiment is approximately 5 cm. As described in the '457 application, a spatial registration system that can detect transducer position along the vessel allows measurements along the entire acquired vessel which can be combined to determine an atheroma volume. It is important to note that natural tortuosity of the vessel may prevent uniform sampling of the vessel along the vessel's longitudinal axis after the polar transformation. This is because specific parts of the perimeter may move at non-uniform spatial distances relative to the longitudinal axis of the vessel. Therefore, prior to calculation of the IMV, in some embodiments, the longitudinal axis of the vessel is remapped to a line segment. The 3D spatial information and temporal information is used to perform the remapping from one coordinate system to the line segment. In the same embodiment, the calculated MAB, LIB, or IMT is remapped to a uniformly sampled line segment using localized 3D weighting technique (e.g. 3D spline).

These methods enable the calculation of the IMV along the detected vessel of interest. In some embodiments, regularization is completed between different acquisition longitudinal positions along the vessel since the lumen center may not have smooth transition. It is important to note that any distribution spread in the MAB for one transducer hold position is suggestive of an atheroma. In this embodiment, regularization is also applied to the MAB, LIB and IMT data. In another embodiment, a non-uniform mesh is created along the longitudinal axis based on the acquisition and vessel 3D position. In this embodiment, the disclosed apparatus determines the optimal mesh size to use for the IMV calculation. If the distances between elements in the mesh are significantly larger than the required value based on transducer performance, then in some embodiments, the apparatus gives a warning to the operator. In another embodiment, the apparatus stops the IMV calculation and suggests to the operator to re-acquire ultrasound data.

The IMV is a calculation of the following integrals:

$$IMV = \frac{1}{2} * [\int_{a1}^{a2} \int_0^{2\pi} ([MAB(\varphi,z)]^2 - [LIB(\varphi,z)]^2) d\varphi dz]$$

where a1 is the starting position along the vessel longitudinal axis (e.g., near the clavicular notch in the case of extracranial carotid) and a2 is the ending position of the acquisition after the bifurcation and the bulb. '$\varphi$' is the angle around the perimeter. Intima-Media Area (IMA) for each position along the vessel longitudinal axis is calculated as:

$$IMA = \frac{1}{2} * [\int_0^{2\pi} ([MAB(\varphi,z)]^2 - [LIB(\varphi,z)]^2) d\varphi]$$

This calculation enables unusual narrowing along the vessel to be easily identified.

The method of integrating multiple spatially registered frames increases the sensitivity and specificity of the measurement and further eliminates false negative and false positives in just one data set. IMV and IMA go beyond the traditional IMT measurement which is done on independent 2D data and expands the assessment to 3D data for an entire cardiac cycle for a more holistic approach to detection of an atheroma.

Results Reporting

IMV

Figure 29A:
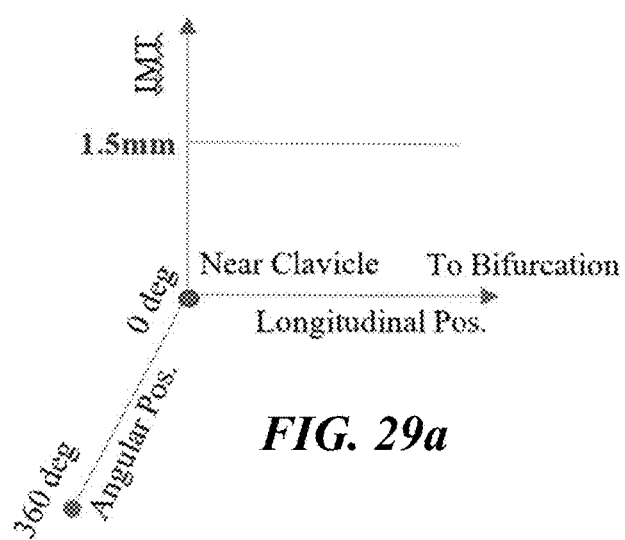
FIGS. 29a-e illustrate multiple ways to display calculated IMT, IMA or IMV data.
Figure 29B:
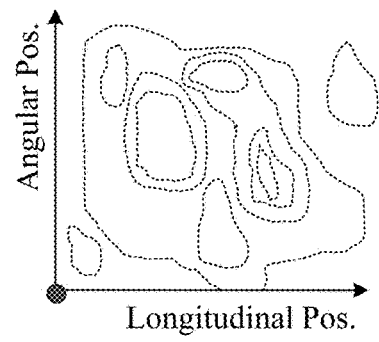
Figure 29C:
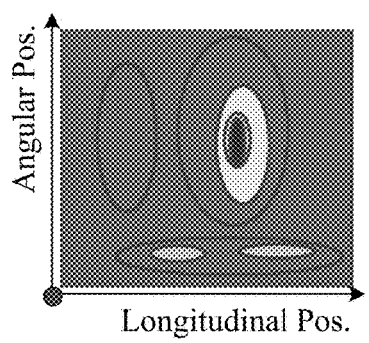
Figure 29D:
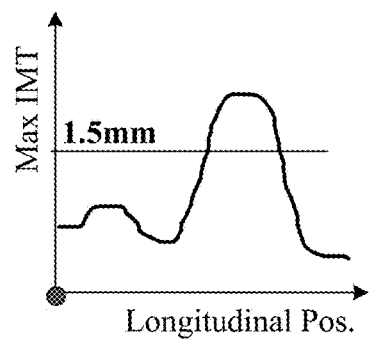
Figure 29E:
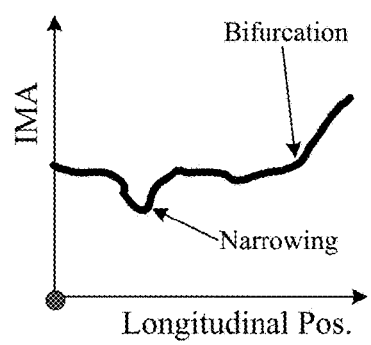

The preceding paragraphs described the calculations of IMV and IMA along the longitudinal axis of the detected vessel of interest which may twist, turn and bifurcate. The calculated IMT, IMA or IMV data can be displayed in multiple ways as illustrated in FIGS. 29a-e for the case of extracranial carotid. In some embodiments, the disclosed apparatus generates a three-dimensional rendered graph to show the measurements or the differences (FIG. 29a). In some embodiments, the apparatus generates a contour graph where the axes are the longitudinal and angular positions and the contours shows the measurements or difference between the media-adventitia and lumen-intima (FIG. 29b). In some embodiments, the apparatus generates a colormap (or a grayscale map) where the axes are the longitudinal and angular positions and the contours shows the measurements or difference between the media-adventitia and lumen-intima (FIG. 29c). In some embodiments, the apparatus generates a max IMT graph where the axes are the longitudinal and angular positions and the contours shows the measurements or difference between the media-adventitia and lumen-intima (FIG. 29d). In another embodiment, the IMA is graphed as a function of longitudinal position (FIG. 29e).

In some embodiments, the apparatus calculates the IMV based on the carotid diameter and integrated along the longitudinal length.

Figure 30:
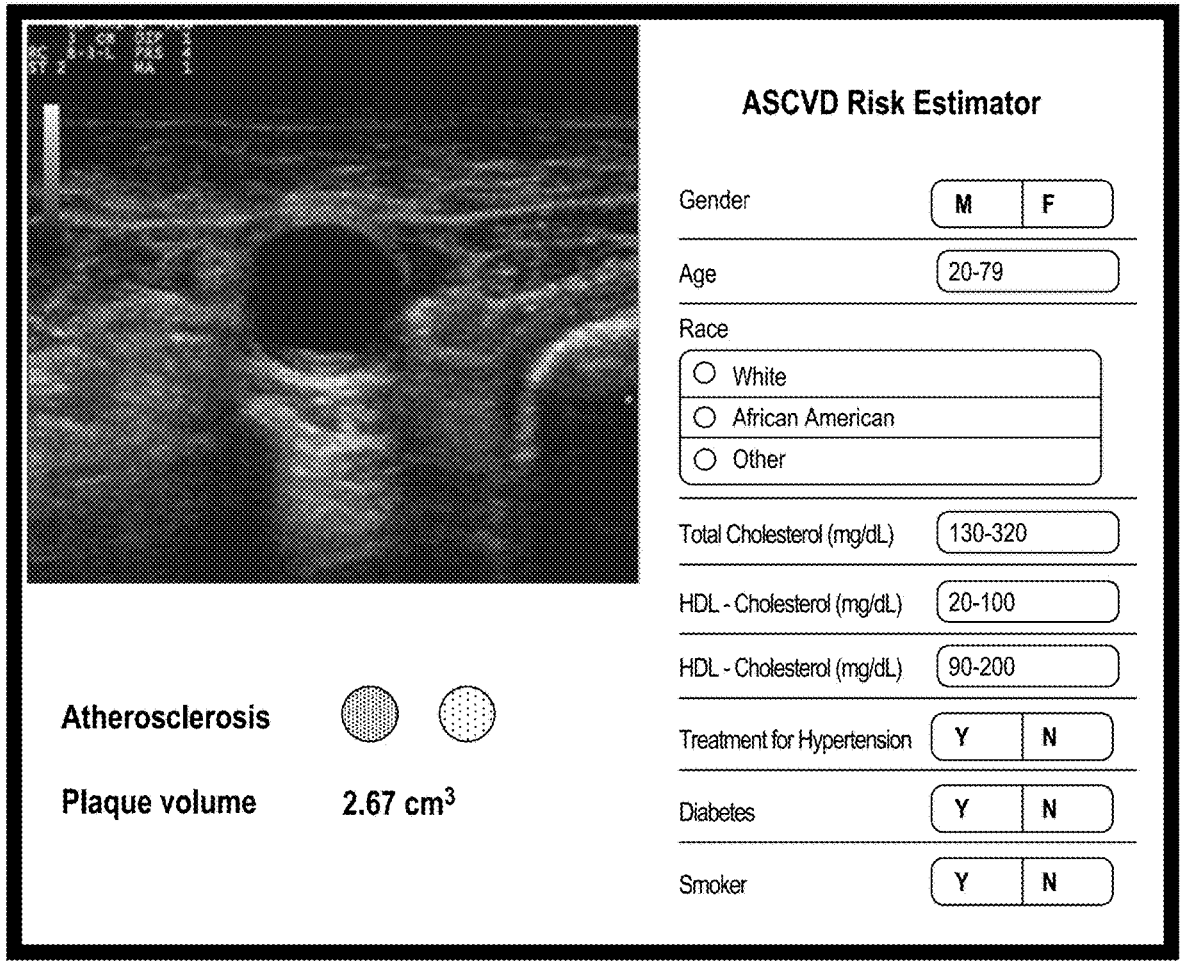
FIG. 30 illustrates an embodiment of a user interface (UI) for a clinical decision-making tool to provide healthcare providers or physicians with a determination whether an atheroma has been detected and the status of other key measures.

FIG. 29. a) Three-dimensional rendered graph b) Contour graph c) Colormap graph d) Max IMT graph e) IMA versus longitudinal position Output User Interface Configurations FIG. 30 shows one exemplary embodiment of a user interface (UI) 3000 with the clinical decision-making tool to provide healthcare providers or physicians with a determination whether an atheroma has been detected and the status of other key measures. In some embodiments, it provides a recommendation to the physician as to whether a patient would benefit from medical intervention in addition to lifestyle intervention for the prevention of atherosclerotic cardiovascular disease. The disclosed apparatus uses a processor to compare published traditional risk factor (TRF) assessment guidelines with ultrasound imaging data from peripheral arteries to produce a display with an easy to interpret recommendation for the physician. The apparatus also displays an estimate of IMV 3010 of detected arteries that is derived from the data sets previously described to assess therapeutic effectiveness by comparing current data with historical measures. In some embodiments, the user interface displays an image of a vessel 3030 including a section of detected atheroma. Such a section can be the thickest section detected or can include an image of the vessel at a set location such as the artery bifurcation.

In some embodiments, the apparatus combines traditional risk factor (TRF) assessment as illustrated in FIG. 31 with ultrasound findings to yield a holistic assessment. In another embodiment, a control is provided to allow the operator to select TRF assessment guideline based on personal preference and geographical location (e.g. US based ACC/AHA Pooled Cohort Equations, European SCORE Project developed by the European Society of Cardiology, Canadian CVD Risk Calculator). In yet another embodiment, the disclosed apparatus provides a summary of the selected TRF in combination with ultrasound findings to determine final recommendation about appropriate intervention as follows:

If TRF is positive but Atheroma is not detected→Recommend lipid lowering therapy If TRF is negative but Atheroma is detected→Recommend lipid lowering therapy and annual ultrasound follow-up If TRF is negative and Atheroma is not detected→Recommend lifestyle changes In another embodiment, the apparatus stores baseline IMV that can be recalled for comparison purposes during subsequent patient visits to determine any changes. If IMV increases by more than a predefined threshold, the care provider is alerted for possible adjustments to therapeutic regimen.

Atheroma Detection (Probability, Location, Length, Volume)

The analyzed ultrasound data vastly improves the ability of medical caregivers to identify, locate, and rank an atheroma during a current acquisition and compare changes to previous acquisitions. This ability is driven by the fact the data is spatially and temporally registered with identifying features such as the bifurcation and bulb. In some embodiments, the probability of the existence of an atheroma is ascertained by the overall atheroma size, length, volume, and average thickness when compared to the overall sensitivity of the apparatus. The location of the detected atheroma is referenced with respect to known arterial anatomical markers (e.g. arterial bifurcation, bulb of carotid). Since the graphs in FIG. 29 have transformed the vessel longitudinal axis into an orthogonal axis, the location determined in this coordinate system must be transformed back to the anatomical coordinate system. Similarly, the length of the detected atheroma is measured in the transformed system. Since the atheroma is of irregular shape, the length could be given as a maximum or average length where the average is based on the contiguous region of the atheroma where the detected intima-media thickness is greater than 1.5 mm. The volume of the atheroma is determined based on an allowable IMT surrounding the detected atheroma. In some embodiments, the allowable IMT is based on known-good vessel regions. In another embodiment, the allowable IMT is set to 1.5 mm. In yet another embodiment, the allowable IMT is based on the median or mean of the IMT histogram along with a one-sided variance. In any case, the volume of the atheroma is determined as a contiguous region where the IMT is above a specified value. In some embodiments, the detected object must satisfy specific lengths and locations to satisfy atheroma criteria. In some embodiments, an atheroma burden is based on measurements of more than one vessel such as the left and right carotids and left and right femoral arteries.

Arterial Diameter and Volume Per Cardiac Cycle

Figure 32:
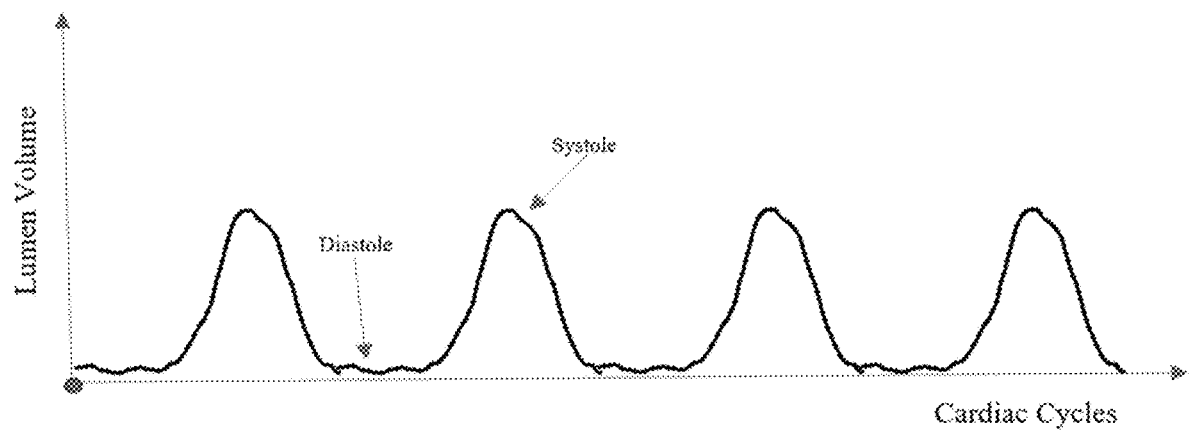
FIG. 32 illustrates measured volume ejected through an acquired vessel as a function of time.

As previously mentioned, the ultrasound data sets are temporally and spatially registered. The cardiac rhythm enables the alignment of the data for different transducer positions to the cardiac cycle. In some embodiments, the temporal alignment along with the lumen identification enables the calculation of the luminal volume throughout the cardiac cycle (e.g., intra-cardiac-cycle) as well calculation of the luminal volume during subsequent cardiac cycles per cycle (e.g., inter-cardiac-cycle). The luminal diameter and overall arterial diameter are close to their respective maxima during systole and close to their respective minima during diastole. Conversely, the intima-media thickness is close to its minimum during systole and close to its maximum during diastole. Knowledge about cardiac cycle timing is therefore automatically and continuously detected by tracking the changes in luminal volume, arterial volume, arterial diameter, luminal diameter as well as intima-media thickness. For illustrative purposes, a graph of luminal volume change over multiple cardiac cycles is shown in FIG. 32. In some embodiments, arterial diameter change during the cardiac cycle is calculated and displayed. In another embodiment, the arterial volume change with cardiac cycle is calculated and displayed. In yet another embodiment, changes during the cardiac cycle in intima-media thickness of the artery of interest is calculated and displayed. Temporal changes in luminal diameter, arterial diameter, luminal volume, arterial volume and intima-media thickness provide clinically relevant physiological information about cardiovascular disease process in addition to the morphological information provided by atheroma detection based on measurements of intima-media thickness, intima-media area and intima-media volume.

Therapeutic Effectiveness of Atheroma Treatment

It is expected that, over time, the disclosed method of arterial scanning will become as important as TRF assessment in the determining whether the primary care physician recommends a cholesterol lowering therapy. In fact, it may eventually replace the conventional methods. Therefore, just as retrospective tracking is important to monitoring patient health, it is expected that comparison to previous studies procedures will be important which helps alert the primary care physician to any suspected changes in arterial health. In some embodiments, this is accomplished through a difference method of two scans procedures taken at separate times and a display of any changes in IMT along the entire longitudinal axis of an artery of interest. In other embodiments, changes in IMV are tracked and compared to baseline data. Predefined thresholds check reproducibility to determine whether a difference in the IMT or IMV is clinically significant. This difference method is provided to assist the primary care physician in determining whether a specific therapy is working or if other preventative measures need to be made. An increase in IMV or focally elevated IMT is indicative of atheroma progression. Conversely, a decrease in IMV or focally elevated IMT is suggestive or atheroma regression. As previously mentioned, in some embodiments, arterial anatomical markers such as the bifurcation or bulb are used to spatially register two different 3D acquisitions. The bifurcation is used for coarse registration whereas the entire length of the scan is used for fine tuning the registration through an error minimization and correlation methods. This is done with the 3D volume data set prior to the determination of the contours since this reduces image contrast that can eliminate key identifying features in each plane.

Example Embodiments

The following is a list of exemplary embodiments of the present technology.

Example 1: A method for detecting the presence of an atheroma in an artery of interest using an ultrasound apparatus, the method comprising: performing a first procedure on a first day, the first procedure comprising—detecting one or more blood vessels in a target region of a patient's body; identifying, from the one or more blood vessels, an artery of interest; automatically detecting spatial boundaries of constituent layers of an arterial wall of the artery of interest and calculating, via a processor of the ultrasound apparatus, a cross-sectional intima-media area (IMA) of the artery of interest at a first location along a length of the artery of interest; automatically calculating, via the processor of the ultrasound apparatus; IMA of the artery of interest at a second or more locations along the length of the artery of interest; and automatically calculating, via the processor and based at least in part on the calculations of the IMAs of the artery of interest at the first location and at the second or more locations, an intima-media volume (IMV), arterial volume, and luminal volume of the artery of interest over a predetermined length of the artery of interest.

Example 2: The method of example 1, further comprising: performing a second procedure on a subsequent day, the second procedure comprising—detecting one or more blood vessels in the target region of a patients body; identifying, from the one or more blood vessels, the artery of interest; automatically detecting spatial boundaries of constituent layers of an arterial wall of the artery of interest and calculating, via the processor of the ultrasound apparatus, an IMA of the artery of interest at a first location along the length of the artery of interest; automatically calculating, via the processor of the ultrasound apparatus, an IMA of the artery of interest at a second or more locations along the length of the artery of interest; and automatically calculating, via the processor and based at least in part on the calculations of IMAs of the artery of interest at the first location and at the second or more locations, the IMV, arterial volume, and luminal volume of the artery of interest over the predetermined length of the artery of interest; and comparing the IMV of the artery of interest measured during the first procedure with the IMV of the artery of interest measured during the second procedure.

Example 3: The method of example 2, further comprising, based at least in part on the comparison between the IMV of the artery of interest measured during the first and second procedures, determining a change in the IMV of the artery of interest associated with progression or regression of an atheroma.

Example 4: The method of any of examples 1-3, wherein the predetermined length of the artery of interest includes anatomical markers for registering a coordinate system in the artery of interest to enable accurate comparisons of measurements between first and subsequent procedures.

Example 5: The method of example 4, wherein one of the anatomical markers is a bifurcation detected by skeletonizing the artery of interest.

Example 6: The method of examples 4 or 5, wherein the anatomical marker is a localized increase in diameter of the artery of interest.

Example 7: The method of any of examples 1-6, wherein identifying blood vessels and artery of interest comprises a machine learning method of neural network trained to identify vessels in ultrasound echography images by using self-derived features and standard vessel characteristics.

Example 8: The method of any of examples 1-6, wherein identifying blood vessels and the artery of interest comprises deterministic methods using known anatomical attributes of vessels.

Example 9: The method of example 8, wherein detecting one or more blood vessels comprises automatically identifying at least one vessel characteristic as detected via ultrasound echo data.

Example 10: The method of examples 8 or 9, wherein detecting one or more blood vessels comprises identifying, via the processor, blood flow data as represented by a color map of Doppler signal analysis.

Example 11: The method of any of examples 8-10, wherein detecting one or more blood vessels comprises, via the processor, correlating frame-to-frame RF data and combining it with a noise map.

Example 12: The method of any of examples 7-11, wherein at least one vessel characteristic includes vessel wall brightness.

Example 13: The method of any of examples 7-12, wherein the at least one vessel characteristic includes vessel wall elastic properties.

Example 14: The method of any of examples 7-13, wherein the at least one vessel characteristic includes vessel pulsatility.

Example 15: The method of any of examples 7-14, wherein the at least one vessel characteristic includes vessel cross-sectional diameter.

Example 16: The method of any of examples 7-15, wherein the at least one vessel characteristic includes vessel location in spatially registered data sets.

Example 17: The method of any of examples 7-16, wherein the at least one vessel characteristic includes blood flow dynamics.

Example 18: The method of any of examples 7-17, wherein the at least one vessel characteristic includes correlation of RF data showing speckle decorrelation.

Example 19: The method of any of examples 7-18, wherein the at least one vessel characteristic includes the identification of a vessel bifurcation when present.

Example 20: The method of any of examples 7-19, wherein the at least one vessel characteristic includes the localized increase in vessel diameter proximal to a bifurcation when present.

Example 21: The method of any of examples 8-11, wherein the artery of interest is detected by identifying a vessel that has diameter and depth within a specific range.

Example 22: The method of any of examples 8-11 or 21, wherein the artery of interest is detected by creating vessel skeletons and identifying vessels that may bifurcate or have a bulb.

Example 23: The method of any of examples 8-11, 21, or 22, wherein the artery of interest is detected by analyzing vessel pulsatility.

Example 24: The method of any of examples 8-11 or 21-23, wherein the artery of interest is detected by tracking vessels through a 3D dataset using frame-to-frame RF correlation.

Example 25: The method of any of examples 1-24, further comprising automatically detecting and tracking, via the processor, an approximate center of the artery of interest as observed along the length of the vessel of interest.

Example 26: The method of example 25, further compromising automatic image acquisition optimization.

Example 27: The method of example 26, further compromising dynamic transmit foci selection.

Example 28: The method of any of examples 26 or 27, further compromising dynamic receive foci selection.

Example 29: The method of any of examples 26-28, further compromising dynamic transmit aperture selection.

Example 30: The method of any of examples 26-29, further compromising dynamic receive aperture selection.

Example 31: The method of any of examples 26-30, further compromising dynamic selection of the optimal number of transmit and receive vectors.

Example 32: The method of any of examples 26-31, further compromising dynamic selection of the optimal field of view (FOV).

Example 33: The method of any of examples 26-32, further creating virtual 2D planes out of the 3D dataset to ensure contiguous inter-frame alignment perpendicular to the vessel axis.

Example 34: An apparatus for detecting the presence of an atheroma in a subject, comprising: an ultrasound transmitter configured to deliver ultrasound to a region of interest with one or more different transmit parameters and to detect return echo signals; processing electronics configured to convert the return echo signals into digital return echo data; a memory configured to store the return echo data; and a processor configured to analyze the stored echo data to detect the presence of one or more blood vessels in surrounding tissue; wherein: the processor is configured to detect the presence of one or more blood vessels by: analyzing specific signal characteristics that identify an arterial vessel of interest; dynamically optimizing return echoes to selectively enhance detection of arterial wall layers; using a detected location of the vessel to select return echo data obtained with transmit parameters that allow for estimating thickness of vessel wall constituent layers at one or more positions along a length of the vessel; and the processor is configured to present an indication to a user of a multi-dimensional summation of measurements of the thickness of vessel wall constituent layers.

Example 35: The apparatus of example 34, wherein the processor is configured to automatically interpret anatomical measurements to determine the presence of an atheroma.

Example 36: The apparatus of examples 34 or 35 wherein detection of atheroma is combined with traditional risk factor assessment to automatically interpret clinical guidelines and present a recommendation to the user on how the subject should be treated.

Example 37: The apparatus of any of examples 34-36, wherein the processor is configured to automatically improve wall detection of the artery if interest.

Example 38: The apparatus of any of examples 34-37, wherein the processor is configured to detect a slope of a vessel wall in the stored echo data and to use the detected slope of the vessel wall to select stored ultrasound data with a transmit direction that is closer to normal to the vessel wall.

Example 39: The apparatus of example 38, wherein the processor is configured to extrapolate the detected slope of the vessel wall and to use the detected slope of the vessel wall to select stored ultrasound data with a transmit direction that is closer to normal to the vessel wall.

Example 40: The apparatus of examples 38 or 39, wherein the processor is configured to dynamically segment a wall of the artery of interest and to reconstruct the wall using a fitted ellipse and using the detected slope of the vessel wall to select stored ultrasound data with a transmit direction that is closer to normal to the vessel wall.

Example 41: The apparatus of any of examples 34-40, wherein the processor is configured to determine an ideal acquisition angle by using Doppler effect blood flow dynamics combined with perimeter fitting and extrapolation.

Example 42: The apparatus of any of any of examples 34-41, wherein the processor is configured to determine the ideal acquisition angle by segmenting the artery of interest by lumen speckle statistics.

Example 43: The apparatus of any of examples 34-42, wherein the processor is configured to acquire ultrasound echo data from the artery of interest with multiple steering angles within a frame.

Example 44: The apparatus of any of examples 34-43, wherein the processor is configured to determine a blood vessel volume of the artery of interest based at least in part on the multi-dimensional summation of measurements of the thickness of vessel wall constituent layers.

Example 45: A method of detecting the presence of an atheroma, the method comprising: delivering ultrasound to a region of a patient's body using an ultrasound transmitter; detecting return echo signals from the delivered ultrasound via the ultrasound transmitter; converting the return echo signals to digital return echo data via one or more processors; storing the digital return echo data in one or more memories; identifying a media-adventitia boundary (MAB) of a blood vessel in the region of the patients body by: preprocessing the digital return echo data using one or more of: envelope detection; dynamic range compression; adaptive spatial compounding; and application of a speckle reduction filter; remapping the digital return echo data from cartesian to polar coordinates; detecting a peak in the digital return echo data in polar coordinates; and correlating the peak with an estimated location of an adventitia layer of the blood vessel; and identifying a lumen-intima boundary (LIB) of the blood vessel by: identifying a lumen of the blood vessel using speckle decorrelation; for one or more angular positions around a boundary of the blood vessel, establishing a radial depth with respect to a center of the blood vessel for further data processing, wherein the radial depth at the one or more angular positions is defined between the adventitia layer and the lumen of the blood vessel; and detecting an edge of the lumen using an edge detection algorithm.

Example 46: The method of example 45, further comprising smoothing data associated with the edge of the lumen, Example 47: The method of examples 45 or 46, wherein identifying the LIB of the blood vessel further comprises segmenting the lumen based on intensity of the return echo data.

Example 48: The method of any of examples 45-47, further comprising smoothing data associated with the estimated location of the adventitia layer.

Example 49: The method of any of examples 45-48, wherein identifying a lumen of the blood vessel further comprises detecting a second peak in the digital return echo data in polar coordinates and correlating the second peak with an estimated location of an intima layer of the blood vessel.

Example 50: The method of any of examples 45-49, further comprising repeating the entire method at least two locations along a patient's artery.

Example 51: The method of example 50, further comprising determining a total intima-media volume of the blood vessel by integrating, via the one or more processors, the MAB and LIB at the at least two locations along the patient's artery.

Example 52: The method of any of examples 45-51, further comprising determining, via the one or more processors, an intima-media thickness of the artery at a predetermined temporal location in a cardiac cycle.

Example 53: The method of example 52, further comprising identifying a probability of the existence of an atheroma based on the determination of the intima-media thickness of the artery.

Example 54: The method of any of examples 45-53, further comprising repeating the entire method on two or more different arteries.

Example 55: The method of any of examples 45-54, comprising the detection of physiological changes during the cardiac cycle.

Example 56: The method of example 55, comprising the detection and calculation of intra-cardiac-cycle and inter-cardiac-cycle luminal volume changes.

Example 57: The method of example 55, comprising the detection and calculation of intra-cardiac-cycle and inter-cardiac-cycle arterial wall diameter changes.

Example 58: The method of example 55, comprising the detection and calculation of intra-cardiac-cycle and inter-cardiac-cycle luminal diameter changes.

Example 59: The method of example 55, comprising the detection and calculation of intra-cardiac-cycle and inter-cardiac-cycle arterial volume changes.

Example 60: The method of example 55, comprising the detection and calculation of intra-cardiac-cycle and inter-cardiac-cycle intima-media thickness changes.

CONCLUSION

The above Detailed Description of examples and embodiments of the inventions is not intended to be exhaustive or to limit the inventions to the precise form disclosed above. Although specific examples for the inventions are described above for illustrative purposes, various equivalent modifications are possible within the scope of the inventions, as those skilled in the relevant art will recognize.

References throughout the foregoing description to features, advantages, or similar language do not imply that all of the features and advantages that may be realized with the present technology should be or are in any single embodiment of the inventions. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment.

Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

Any patents and applications and other references noted above, including any that may be listed in accompanying filing papers, are incorporated herein by reference. Aspects of the inventions can be modified, if necessary, to employ the systems, functions, and concepts of the various references described above to provide yet further implementations of the inventions.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the inventions provided herein can be applied to other systems, not necessarily the system described above. The elements and acts of the various examples described above can be combined to provide further implementations of the inventions. Some alternative implementations of the inventions may include not only additional elements to those implementations noted above, but also may include fewer elements. Further any specific numbers noted herein are only examples: alternative implementations may employ differing values or ranges.

Although the above description describes various embodiments of the inventions and the best mode contemplated, regardless how detailed the above text, the inventions can be practiced in many ways. Details of the systems, methods, and apparatuses may vary considerably in its specific implementation, while still being encompassed by the present technology. As noted above, particular terminology used when describing certain features or aspects of the inventions should not be taken to imply that the terminology is being redefined herein to be restricted to any specific characteristics, features, or aspects of the inventions with which that terminology is associated. In general, the terms used in the following claims should not be construed to limit the inventions to the specific examples disclosed in the specification, unless the above Detailed Description section explicitly defines such terms. Accordingly, the actual scope of the inventions encompasses not only the disclosed examples, but also all equivalent ways of practicing or implementing the inventions under the claims.

From the foregoing, it will be appreciated that specific embodiments of the inventions have been described herein for purposes of illustration, but that various modifications may be made without deviating from the spirit and scope of the various embodiments of the inventions. Further, while various advantages associated with certain embodiments of the inventions have been described above in the context of those embodiments, other embodiments may also exhibit such advantages, and not all embodiments need necessarily exhibit such advantages to fall within the scope of the inventions. Accordingly, the inventions are not limited, except as by the appended claims.

Although certain aspects of the inventions are presented below in certain claim forms, the applicant contemplates the various aspects of the inventions in any number of claim forms. Accordingly, the applicant reserves the right to pursue additional claims after filing this application to pursue such additional claim forms, in either this application or in a continuing application.

We claim:

1. A method for detecting a presence of an atheroma using an ultrasound apparatus, the method comprising:
   performing a procedure comprising—
   repeatedly obtaining echo signals produced in response to ultrasound signals generated via a transducer;
   based on the obtained echo signals, producing ultrasound image data via processing circuitry;
   detecting, via the processing circuitry and without user input, a volume of interest and one or more blood vessels from the ultrasound image data in a target region of a patient's body as the echo signals are being obtained;
   identifying, via the processing circuitry and from the one or more blood vessels, an artery of interest based on:
   a brightness of a wall of the artery of interest,
   a darkness in a lumen of the artery of interest, and
   a difference between the brightness of the artery wall and the darkness of the artery lumen;
   tracking the artery of interest via radio frequency (RF) correlation of contiguous 2-dimensional (2D) frames of a 3D dataset, wherein the 2D frames include at least a first frame, a second frame, and a third frame, and wherein a tracked length of the artery of interest encompasses at least a segment of a common carotid region of the carotid artery of the patient and a bifurcated region of the carotid artery;
   determining via cross-correlation of the first frame to the second frame, the first frame to the third frame, and the second frame to the third frame, that each of the first frame, the second frame, and the third frame include the artery of interest;
   identifying an atheroma in the artery of interest;
   obtaining a plurality of intima-media thicknesses (IMTs) along a longitudinal axis of the artery of interest, wherein each of the IMTs is based on a distance between edges of (i) a first peak of a first echo signal corresponding to a media-adventitia boundary and (ii) a second peak corresponding to a lumen-intima boundary;

based at least in part on the obtained IMTs, calculating, via the processing circuitry, a first cross-sectional intima-media area (IMA) of the artery of interest at a first location along a length of the artery of interest;

based at least in part on the obtained IMTs, calculating, via the processing circuitry, a second IMA of the artery of interest at a second or more locations along the length of the artery of interest; and based at least in part on the calculations of the first and second IMAs of the artery of interest, calculating, via the processing circuitry, an intima-media volume (IMV), arterial volume, and luminal volume of the artery of interest over a predetermined length of the artery of interest.

2. The method of claim 1, wherein the length of the artery of interest includes one or more anatomical markers for registering a coordinate system in the artery of interest to enable accurate comparisons of measurements between first and subsequent procedures.

3. The method of claim 2, wherein at least one of the one or more anatomical markers is a bifurcation detected by skeletonizing the artery of interest.

4. The method of claim 2, wherein at least one of the one or more anatomical marker is a localized increase in diameter of the artery of interest.

5. The method of claim 1, wherein identifying the artery of interest comprises utilizing a machine learning method of neural network trained to identify vessels in ultrasound echography images by using self-derived features and standard vessel characteristics.

6. The method of claim 1, wherein identifying the artery of interest comprises utilizing deterministic methods using known anatomical attributes of vessels.

7. The method of claim 1 wherein detecting the one or more blood vessels comprises identifying at least one vessel characteristic without user input.

8. The method of claim 1, wherein detecting the one or more blood vessels comprises identifying, via the processor, blood flow data as represented by a color map of Doppler signal analysis.

9. The method of claim 1, wherein detecting the one or more blood vessels comprises correlating frame-to-frame radio frequency (RF) data and combining it with a noise map.

10. The method of claim 1, wherein identifying the artery of interest comprises identifying at least one vessel characteristic including vessel wall elastic properties.

11. The method of claim 1, wherein identifying the artery of interest comprises identifying at least one vessel characteristic including vessel pulsatility.

12. The method of claim 1, wherein identifying the artery of interest comprises identifying at least one vessel characteristic including vessel cross-sectional diameter.

13. The method of claim 1, wherein identifying the artery of interest comprises identifying at least one vessel characteristic including vessel location in spatially registered data sets.

14. The method of claim 1, wherein identifying the artery of interest comprises identifying at least one vessel characteristic including blood flow dynamics.

15. The method of claim 1, wherein identifying the artery of interest comprises identifying at least one vessel characteristic including correlation of radio frequency (RF) data showing speckle decorrelation.

16. The method of claim 1, wherein identifying the artery of interest comprises identifying, without user input, at least one vessel characteristic including a vessel bifurcation when present.

17. The method of claim 1, wherein identifying the artery of interest comprises identifying at least one vessel characteristic including a localized increase in vessel diameter.

18. The method of claim 1, wherein identifying the artery of interest comprises identifying a vessel that has diameter and depth within a predetermined range.

19. The method of claim 1, wherein identifying the artery of interest comprises creating vessel skeletons and identifying vessels that bifurcate or have a bulb.

20. The method of claim 1, wherein identifying the artery of interest comprises analyzing vessel pulsatility.

21. The method of claim 1, wherein identifying the artery of interest comprises tracking vessels through a 3D dataset using frame-to-frame radio frequency (RF) correlation.

22. The method of claim 1, further comprising spatially relocating the transducer, wherein tracking the artery of interest occurs as the transducer is spatially relocated.

23. A method for detecting a presence of an atheroma using an ultrasound apparatus, the method comprising:

repeatedly obtaining echo signals produced in response to ultrasound signals generated via a transducer;

based on the obtained echo signals, producing ultrasound image data via processing circuitry;

detecting, without user input and via the processing circuitry, one or more blood vessels from the ultrasound image data at a target region of a patient;

identifying, without user input and via the processing circuitry, an artery of interest from the one or more blood vessels as the echo signals are being obtained by (i) creating a 3D dataset of the one or more blood vessels using radio frequency (RF) correlation, and (ii) creating virtual 2-dimensional (2D) frames out of the 3D dataset, wherein the 2D frames include at least a first frame, a second frame, and a third frame, and wherein the artery of interest includes at least two of (i) a bulb of the carotid artery of the patient, (ii) a bifurcation of the carotid artery, or (iii) a common carotid region of the carotid artery, wherein identifying the artery of interest is based on (i) a brightness of a wall of the artery, (ii) a darkness in a lumen of the artery, and (iii) a difference between the brightness of the artery wall and the darkness of the artery lumen;

determining via cross-correlation of the first frame to the second frame, the first frame to the third frame, and the second frame to the third frame, that each of the first frame, the second frame, and the third frame include the artery of interest;

identifying an atheroma in the artery of interest;

obtaining a plurality of intima-media thicknesses (IMTs) along a longitudinal axis of the artery of interest, wherein each of the IMTs is based on a distance between (i) an edge of a first peak of a first echo signal corresponding to a media-adventitia boundary and (ii) an edge of a second peak of a second echo signal corresponding to a lumen-intima boundary;

based on the obtained IMTs, obtaining (i) a first intima-media area (IMA) of the artery of interest at a first location of the artery of interest and (ii) a second IMA of the artery of interest at a second location different than the first location; and based at least in part on the first IMA and the second IMA, calculating an intima-media volume (IMV) of the artery of interest over a predetermined length of the artery of interest.

24. The method of claim 23, wherein identifying the artery of interest occurs at a first time and wherein the IMV is a first IMV, the method further comprising:
identifying the artery of interest from the one or blood vessels at a second time after the first time;
obtaining a third IMA of the artery of interest at a third location of the artery of interest;
obtaining a fourth IMA of the artery of interest at a fourth location different than the third location; and
based at least in part on the third IMA and the fourth IMA, obtaining a second IMV of the artery of interest over a predetermined length of the artery of interest; and
comparing the first IMV with the second IMV to determine progression or regression of atherosclerosis.

25. The method of claim 23, further comprising detecting physiological changes associated with the cardiac cycle of the patient, wherein obtaining the first IMA and/or obtaining the second IMA is based at least in part on the detected physiological changes associated with the cardiac cycle of the patient.

26. The method of claim 25, wherein detecting the physiological changes comprising detecting a change in a luminal diameter during an intra-cardiac cycle and/or an inter-cardiac cycle.

27. The method of claim 25, wherein detecting the physiological changes comprising detecting a change in intima-media thickness during an intra-cardiac cycle and/or an inter-cardiac cycle.

28. The method of claim 25, wherein detecting the physiological changes comprising detecting a change in an arterial wall diameter during an intra-cardiac cycle and/or an inter-cardiac cycle.

29. The method of claim 25, wherein detecting the physiological changes comprising detecting a change in arterial volume during an intra-cardiac cycle and/or an inter-cardiac cycle.

30. The method of claim 23, wherein obtaining the IMV comprises obtaining the IMV via the processing circuitry and without user input.

31. The method of claim 23, wherein the IMV corresponds at least in part to a volume of the atheroma.

32. A method for detecting a presence of an atheroma using an ultrasound apparatus, the method comprising:
repeatedly obtaining echo signals produced in response to ultrasound signals generated via a transducer;
based on the obtained echo signals, producing ultrasound image data via processing circuitry;
detecting, without user input and via the processing circuitry, one or more blood vessels from the ultrasound image data at a target region of a patient;
identifying, without user input and via the processing circuitry, an artery of interest from the one or more blood vessels as the echo signals are being obtained by (i) creating a 3D dataset of the one or more blood vessels using radio frequency (RF) correlation, and (ii) creating virtual 2-dimensional (2D) frames out of the 3D dataset, wherein the 2D frames include at least a first frame, a second frame, and a third frame, wherein identifying the artery of interest is based on (i) a brightness of a wall of the artery, (ii) a darkness in a lumen of the artery, and (iii) a difference between the brightness of the artery wall and the darkness of the artery lumen, and wherein a tracked length of the artery of interest encompasses at least a segment of a common carotid region of the carotid artery of the patient and a bifurcated region of the carotid artery;
determining via cross-correlation of the first frame to the second frame, the first frame to the third frame, and the second frame to the third frame, that each of the first frame, the second frame, and the third frame include the artery of interest;
identifying an atheroma in the artery of interest;
obtaining a plurality of intima-media thicknesses (IMTs) along a longitudinal axis of the artery of interest, wherein each of the IMTs is based on a distance between (i) an edge of a first peak of a first echo signal corresponding to a media-adventitia boundary and (ii) an edge of a second peak of a second echo signal corresponding to a lumen-intima boundary;
based on the obtained IMTs, obtaining (i) a first intima-media area (IMA) of the artery of interest at a first location of the artery of interest and (ii) a second IMA of the artery of interest at a second location different than the first location; and
based at least in part on the first IMA and the second IMA, calculating an intima-media volume (IMV) of the artery of interest over a predetermined length of the artery of interest.

* * * * *

UNITED STATES PATENT AND TRADEMARK OFFICE
CERTIFICATE OF CORRECTION

| | |
|---|---|
| PATENT NO. | : 12,268,552 B2 |
| APPLICATION NO. | : 17/084299 |
| DATED | : April 8, 2025 |
| INVENTOR(S) | : Ram L. Bedi et al. |

It is certified that error appears in the above-identified patent and that said Letters Patent is hereby corrected as shown below:

On the Title Page

On the page 3, in Column 1, item (56) under "Other Publications", Line 12, delete "Guassian" and insert -- Gaussian --.

On the page 3, in Column 1, item (56) under "Other Publications", Line 33, after "novel" delete "of".

On the page 3, in Column 2, item (56) under "Other Publications", Line 10, delete "humad" and insert -- human --.

On the page 3, in Column 2, item (56) under "Other Publications", Line 31, delete "inti ma" and insert -- intima --.

In the Specification

In Column 2, Line 38, delete "atheroma" and insert -- atheroma. --.

In Column 2, Line 62, delete "patients" and insert -- patient's --.

In Column 7, Line 40, delete "atheroma," and insert -- atheroma. --.

In Column 7, Line 60, delete "methods," and insert -- methods. --.

In Column 9, Line 11, delete "carotid," and insert -- carotid. --.

In Column 9, Line 66, before "a" delete "the".

In Column 14, Line 32, delete "e.g.;" and insert -- e.g., --.

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 12,268,552 B2

In Column 14, Line 44, delete "artifacts;" and insert -- artifacts, --.

In Column 17, Line 15, delete "$w(\theta_i)=\cos(\theta_S-\theta_i)$" and insert -- $w(\theta_i)=\cos(\theta_s-\theta_i)$ --.

In Column 17, Line 40, delete "cm," and insert -- cm. --.

In Column 17, Line 59, delete "data" and insert -- data. --.

In Column 18, Line 1, delete "Similarly;" and insert -- Similarly, --.

In Column 19, Line 8, delete "carotid" and insert -- carotid. --.

In Column 19, Line 10, delete "time" and insert -- time. --.

In Column 21, Line 7, delete "Trans," and insert -- Trans. --.

In Column 22, Line 4, after "now" insert -- is from --.

In Column 23, Line 26, delete "6;" and insert -- 6, --.

In Column 23, Line 30, delete "2704," and insert -- 2704. --.

In Column 26, Line 6, delete "position" and insert -- position. --.

In Column 28, Line 52, delete "patients" and insert -- patient's --.

In Column 31, Line 31, delete "any of any of" and insert -- any of --.

In Column 31, Line 53, delete "patients" and insert -- patient's --.

In Column 32, Line 6, delete "lumen," and insert -- lumen. --.